(12) United States Patent
Schnarr et al.

(10) Patent No.: US 10,770,196 B2
(45) Date of Patent: Sep. 8, 2020

(54) BINARY MULTILEAF COLLIMATOR DELIVERY WITH PER-LEAF FIELD WIDTH

(71) Applicant: Accuray Incorporated, Sunnyvale, CA (US)

(72) Inventors: Eric Schnarr, McFarland, WI (US); Hari Gopalakrishnan, Milpitas, CA (US); Jari Toivanen, Redwood City, CA (US); Matthew Orton, Oregon, WI (US)

(73) Assignee: ACCURAY INCORPORATED, Sunnyvale, CA (US)

( * ) Notice: Subject to any disclaimer, the term of this patent is extended or adjusted under 35 U.S.C. 154(b) by 0 days.

(21) Appl. No.: 16/056,114

(22) Filed: Aug. 6, 2018

(65) Prior Publication Data

US 2020/0043625 A1 Feb. 6, 2020

(51) Int. Cl.
| | |
|---|---|
| *G21K 1/04* | (2006.01) |
| *A61N 5/10* | (2006.01) |
| *G21K 1/093* | (2006.01) |

(52) U.S. Cl.
CPC .......... *G21K 1/046* (2013.01); *A61N 5/1047* (2013.01); *G21K 1/093* (2013.01)

(58) Field of Classification Search
CPC .............................. G21K 1/046; A61N 5/1047
See application file for complete search history.

(56) References Cited

U.S. PATENT DOCUMENTS

| | | |
|---|---|---|
| 9,443,633 B2 | 9/2016 | Orton et al. |
| 2008/0159478 A1 | 7/2008 | Keall et al. |
| 2014/0239204 A1* | 8/2014 | Orton ..................... G21K 1/046 |
| | | 250/505.1 |
| 2018/0193668 A1 | 7/2018 | Jordan et al. |

OTHER PUBLICATIONS

Unkelbach et al., "Optimization approaches to volumetric modulated art therapy planning", American Association of Medical Physics, vol. 42, No. 3, pp. 1367-1377, Mar. 2015.
Zhang et al., "Development and performance evaluation of a high-speed multileaf collimator", Journal of Applied Clinical Medical Physics, vol. 18, pp. 96-106, 2017.
International Search Report for the International application No. PCT/US2019/045357, dated Nov. 20, 2019.

* cited by examiner

*Primary Examiner* — Eliza W Osenbaugh-Stewart
(74) *Attorney, Agent, or Firm* — Womble Bond Dickinson (US) LLP

(57) ABSTRACT

A radiation treatment delivery system, includes a linear accelerator (LINAC) and a multileaf collimator (MLC), coupled with the distal end of the LINAC, wherein the MLC has two banks of leaves, organized into a plurality of opposing leaf pairs. The system further includes a processing device, operatively coupled to the LINAC and the MLC, to control the plurality of leaf pairs of the MLC such that for each of a plurality of radiation beam delivery positional sections corresponds to a range of radiation beam positions over a discrete time interval, wherein each leaf pair of the plurality of opposing leaf pairs is open to a fixed opening for a fraction of time in the discrete time interval and closed for the remaining fraction of time in the discrete time interval, while a radiation beam of the radiation treatment system is active.

29 Claims, 14 Drawing Sheets

BINARY MULTILEAF COLLIMATOR DELIVERY WITH PER-LEAF FIELD WIDTH

TECHNICAL FIELD

The present disclosure relates to binary multileaf collimator (MLC) delivery with a per-leaf field width in a radiation treatment system.

BACKGROUND

In radiation treatment, doses of radiation delivered via a radiation treatment beam from a source outside a patient's body are delivered to a target region in the body, in order to destroy tumorous cells. Care must be taken to minimize the amount of radiation that is delivered to non-treatment regions while maximizing the amount of radiation delivered to the intended treatment regions. In radiation treatment, a radiation treatment beam aperture shapes the radiation treatment beam to conform, as closely as possible, to the intended target region. The radiation treatment beam aperture is commonly defined by an MLC.

BRIEF DESCRIPTION OF THE DRAWINGS

The present disclosure will be understood more fully from the detailed description given below and from the accompanying drawings of various implementations of the disclosure.

DETAILED DESCRIPTION

Figure 1A:
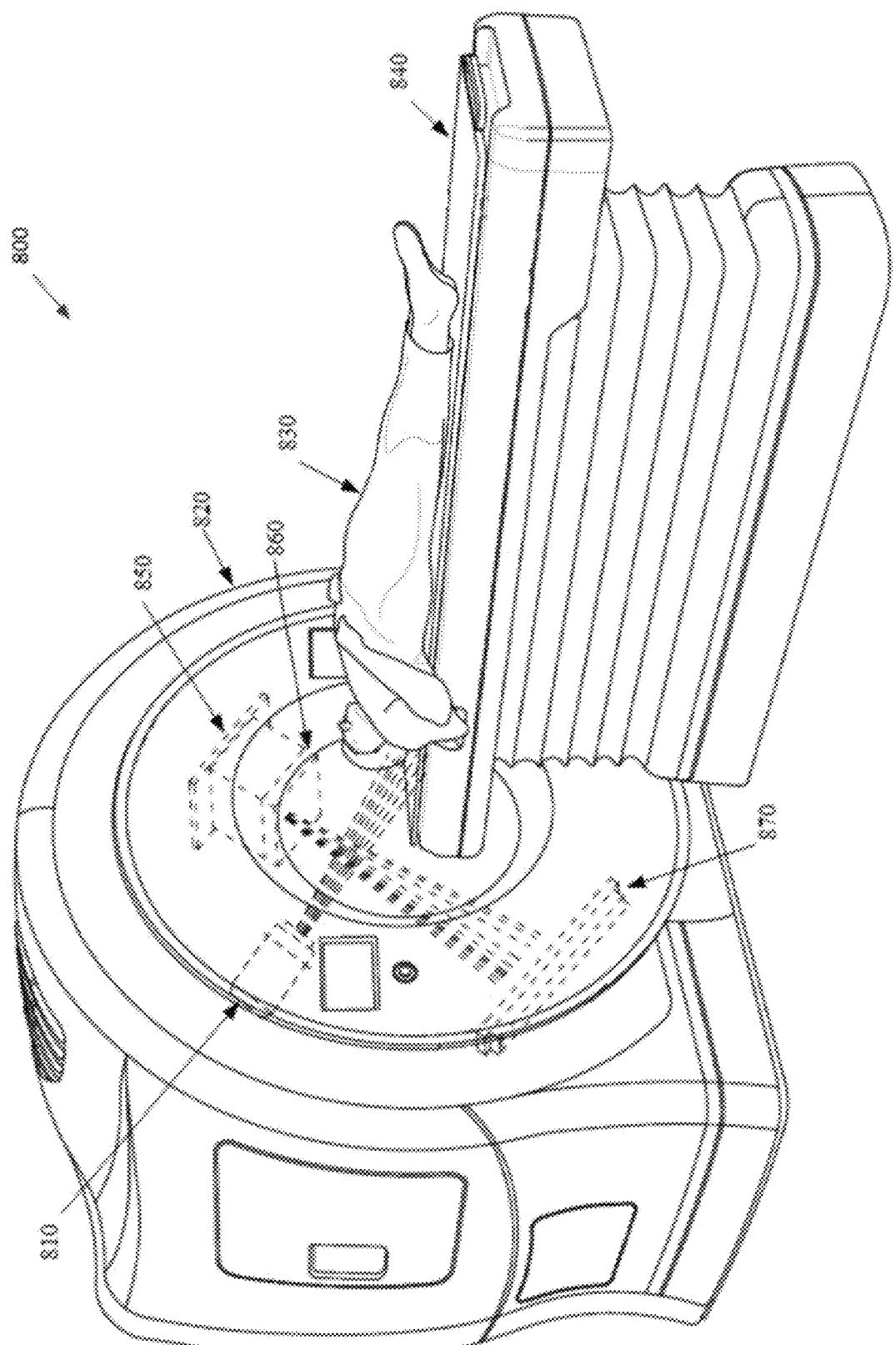
FIG. 1A illustrates a helical radiation delivery system, in accordance with embodiments described herein.

Described herein are embodiments of methods and apparatus for binary MLC radiation treatment delivery with per-leaf field width. In radiation treatment systems, opposing banks of leaves of an MLC may be used to create one or more patterns that shape a radiation treatment beam to conform to a target region.

For target regions with non-uniform shapes, IMRT can be utilized to deliver more complicated radiation treatment doses. Intensity modulated radiotherapy (IMRT) includes a variety of radiation treatment techniques that, essentially, vary the radiation treatment beam intensity that is directed at the target region. In IMRT, rather than having the MLC shape the radiation treatment beam to match a particular outline, the MLC is instead used to create an array of beam shapes that generate a desired intensity modulation and a desired 3D dose distribution via overlapping radiation fields of (possibly) different intensities.

In some embodiments, binary MLCs include a plurality of leaf pairs, arranged in two opposing banks. Each bank of leaves is used to form a treatment slice by positioning the leaf in a closed position or open position with respect to the beam. In some embodiments, the superior-inferior (sup-inf) field width (e.g., the width formed by the openings of the leaf pairs in the MLC) is constant across all leaves of the MLC. Disadvantageously, this means that such systems are incapable of conforming the field of the radiation treatment beam to a target profile along the length of the target. Due to this limitation, field sizes in binary MLCs are generally limited to less than 5 cm. Larger field sizes would generally be undesirable for treating a majority number of target regions, due to the amount of radiation exposure to non-target regions.

One solution to the above problems is to use dynamic jaws to better conform the field to the target region on the superior and inferior ends. Such a technique does not conform the field to the edges of the target along its length, however, because the field size is defined by the jaws and is constant across the entire MLC. Another solution is to use a non-binary, shape-conforming MLC. Such MLCs can be slow, however, which may negatively impact treatment time. Another solution is provided herein.

Advantageously, the embodiments described herein allow an MLC to conform treatment beam fields to target regions, while minimizing radiation exposure to non-treatment regions. Furthermore, the embodiments described herein allow for larger field sizes (e.g., larger than 5 cm), which may increase the speed of treatments. Furthermore, the embodiments described herein allow an MLC to modulate fluence field, not just in the IEC-Xb direction, but also in the IEC-Yb direction, as described herein. Furthermore, the embodiments described herein allow for more opportunities for modulation in the longitudinal direction. This may allow treatment plans to have a looser pitch (e.g., close to 1), where sup-inf modulation is handled by longitudinal modulation of MLC leaves. Alternatively, a tighter pitch may be maintained with additional opportunities to modulate the treatment beam over the same sup-inf region.

The systems and methods described herein accomplish the above advantages via the use of a high-speed MLC. One example, of such a high-speed MLC is an electromagnetic MILC (eMLC), as described herein. It should be noted, however, that alternative variations of a high-speed MLC may be used to perform the operations described herein. For the purposes of the present disclosure, a high-speed MLC may be any MLC that is capable of very fast leaf motion (e.g., approximately able to cross a 5 cm field in less than 100 ms). It should be noted that although "eMLC" is used throughout the present disclosure, the systems and methods described herein are equally compatible with any other form of high-speed MLC.

Furthermore, for the purposes of this description, the terms "fluence," "intensity," and "dose" are used as follows. Fluence is the number of photons or x-rays that crosses a unit of area perpendicular to a radiation beam. Fluence rate is the fluence per unit time. Intensity is the energy that crosses a unit area per unit time. Fluence and intensity are independent of what occurs in a patient, and more specifically are not dose. Dose is the amount of energy absorbed by tissue by virtue of radiation impacting the tissue. Radiation dose is measured in units of gray (Gy), where each Gy corresponds to a fixed amount of energy absorbed in a unit mass of tissue (e.g., 1 joule/kg). Dose is not the same as fluence, but increases/decreases as fluence increases/decreases.

The terms "target" and "target region" may refer to one or more fiducials near (within some defined proximity to) a treatment area (e.g., a tumor). In another embodiment, a target may be a bony structure. In yet another embodiment a target may refer to soft tissue of a patient. A target may be any defined structure or area capable of being identified and tracked, as described herein.

FIG. 1A illustrates a helical radiation delivery system 800 in accordance with embodiments of the present disclosure. The helical radiation delivery system 800 may include a linear accelerator (LINAC) 850 mounted to a ring gantry 820. The LINAC 850 may be used to generate a radiation beam (i.e., treatment beam) by directing an electron beam towards an x-ray emitting target. The treatment beam may deliver radiation to a target region (i.e., a tumor). The treatment system further includes a multileaf collimator (MLC) 860 coupled with the distal end of the LINAC 850. The MLC 860 may be an eMLC, as described herein. The MLC includes a housing that houses multiple leaves that are movable to adjust an aperture of the MLC to enable shaping of the treatment beam. The ring gantry 820 has a toroidal shape in which the patient 830 extends through a bore of the ring/toroid and the LINAC 850 is mounted on the perimeter of the ring and rotates about the axis passing through the center to irradiate a target region with beams delivered from one or more angles around the patient. During treatment, the patient 830 may be simultaneously moved through the bore of the gantry on a treatment couch 840.

The helical radiation delivery system 800 includes an imaging system, comprising the LINAC 850 as an imaging source and an x-ray detector 870. The LINAC 850 may be used to generate a mega-voltage x-ray image (MVCT) of a region of interest (ROI) of patient 830 by directing a sequence of x-ray beams at the ROI which are incident on the x-ray detector 870 opposite the LINAC 850 to image the patient 830 for setup and generate pre-treatment images. In one embodiment, the helical radiation delivery system 800 may also include a secondary imaging system consisting of a kV imaging source 810 mounted orthogonally relative to the LINAC 850 (e.g., separated by 90 degrees) on the ring gantry 820 and may be aligned to project an imaging x-ray beam at a target region and to illuminate an imaging plane of a detector after passing through the patient 130.

Figure 1B:
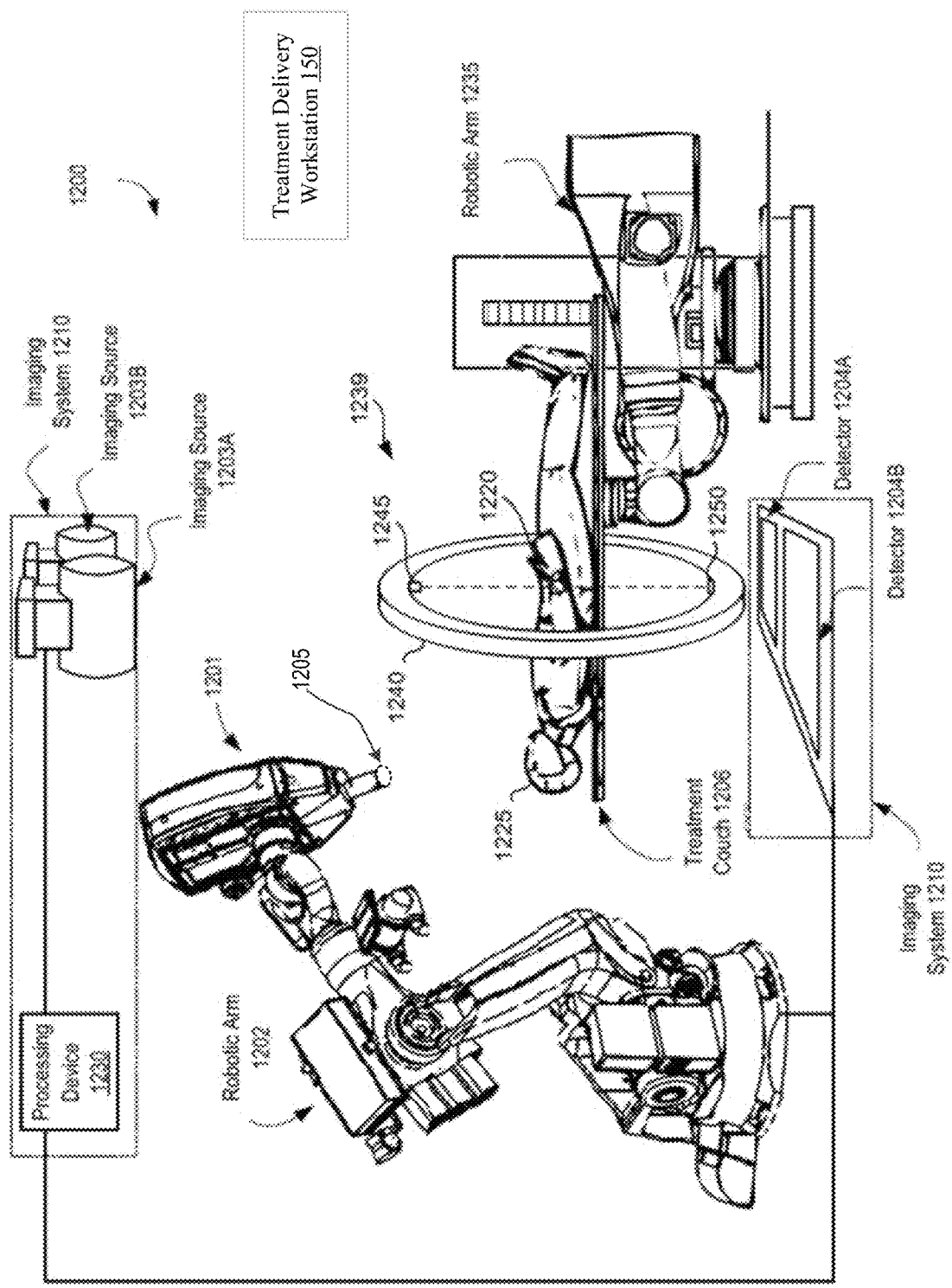
FIG. 1B illustrates a robotic radiation treatment system that may be used in accordance with embodiments described herein.

FIG. 1B illustrates a radiation treatment system 1200 that may be used in accordance with alternative embodiments described herein. As shown, FIG. 1B illustrates a configuration of a radiation treatment system 1200. In the illustrated embodiments, the radiation treatment system 1200 includes a linear accelerator (LINAC) 1201 that acts as a radiation treatment source and an MLC 1205 (e.g., an eMLC) coupled with the distal end of the LINAC 1201 to shape the treatment beam. In one embodiment, the LINAC 1201 is mounted on the end of a robotic arm 1202 having multiple (e.g., 5 or more) degrees of freedom in order to position the LINAC 1201 to irradiate a pathological anatomy (e.g., target) with beams delivered from many angles, in many planes, in an operating volume around a patient. Treatment may involve beam paths with a single isocenter, multiple isocenters, or with a non-isocentric approach.

LINAC 1201 may be positioned at multiple different nodes (predefined positions at which the LINAC 1201 is stopped and radiation may be delivered) during treatment by moving the robotic arm 1202. At the nodes, the LINAC 1201 can deliver one or more radiation treatment beams to a target, where the radiation beam shape is determined by the leaf positions in the MLC 1205. The nodes may be arranged in an approximately spherical distribution about a patient. The particular number of nodes and the number of treatment beams applied at each node may vary as a function of the location and type of pathological anatomy to be treated.

In another embodiment, the robotic arm 1202 and LINAC 1201 at its end may be in continuous motion between nodes while radiation is being delivered. The radiation beam shape and 2-D intensity map is determined by rapid motion of the leaves in the MLC 1205 during the continuous motion of the LINAC 1201.

The radiation treatment system 1200 includes an imaging system 1210 having a processing device 1230 connected with x-ray sources 1203A and 1203B (i.e., imaging sources) and fixed x-ray detectors 1204A and 1204B. Alternatively, the x-ray sources 1203A, 1203B and/or x-ray detectors 1204A, 1204B may be mobile, in which case they may be repositioned to maintain alignment with the target, or alternatively to image the target from different orientations or to acquire many x-ray images and reconstruct a three-dimensional (3D) cone-beam CT. In one embodiment, the x-ray sources are not point sources, but rather x-ray source arrays, as would be appreciated by the skilled artisan. In one embodiment, LINAC 1201 serves as an imaging source, where the LINAC power level is reduced to acceptable levels for imaging.

Imaging system 1210 may perform computed tomography (CT) such as cone beam CT or helical megavoltage computed tomography (MVCT), and images generated by imaging system 1210 may be two-dimensional (2D) or three-dimensional (3D). The two x-ray sources 1203A and 1203B may be mounted in fixed positions on the ceiling of an operating room and may be aligned to project x-ray imaging beams from two different angular positions (e.g., separated by 90 degrees) to intersect at a machine isocenter (referred to herein as a treatment center, which provides a reference point for positioning the patient on a treatment couch 1206 during treatment) and to illuminate imaging planes of respective detectors 1204A and 1204B after passing through the patient. In one embodiment, imaging system 1210 provides stereoscopic imaging of a target and the surrounding volume of interest (VOI). In other embodiments, imaging system 1210 may include more or less than two x-ray sources and more or less than two detectors, and any of the detectors may be movable rather than fixed. In yet other embodiments, the positions of the x-ray sources and the detectors may be interchanged. Detectors 1204A and 1204B may be fabricated from a scintillating material that converts the x-rays to visible light (e.g., amorphous silicon), and an array of CMOS (complementary metal oxide silicon) or CCD (charge-coupled device) imaging cells that convert the light to a digital image that can be compared with a reference image during an image registration process that transforms a coordinate system of the digital image to a coordinate system of the reference image, as is well known to the skilled artisan. The reference image may be, for example, a digitally reconstructed radiograph (DRR), which is a virtual x-ray image that is generated from a 3D CT image based on simulating the x-ray image formation process by casting rays through the CT image.

In one embodiment, IGRT delivery system 1200 also includes a secondary imaging system 1239. Imaging system 1239 is a Cone Beam Computed Tomography (CBCT) imaging system, for example, the medPhoton ImagingRing System. Alternatively, other types of volumetric imaging systems may be used. The secondary imaging system 1239 includes a rotatable gantry 1240 (e.g., a ring) attached to an arm and rail system (not shown) that move the rotatable gantry 1240 along one or more axes (e.g., along an axis that extends from a head to a foot of the treatment couch 1206. An imaging source 1245 and a detector 1250 are mounted to the rotatable gantry 1240. The rotatable gantry 1240 may rotate 360 degrees about the axis that extends from the head to the foot of the treatment couch. Accordingly, the imaging source 1245 and detector 1250 may be positioned at numerous different angles. In one embodiment, the imaging source 1245 is an x-ray source and the detector 1250 is an x-ray detector. In one embodiment, the secondary imaging system 1239 includes two rings that are separately rotatable. The imaging source 1245 may be mounted to a first ring and the detector 1250 may be mounted to a second ring. In one embodiment, the rotatable gantry 1240 rests at a foot of the treatment couch during radiation treatment delivery to avoid collisions with the robotic arm 1202.

As shown in FIG. 1B, the image-guided radiation treatment system 1200 may further be associated with a treatment delivery workstation 150. The treatment delivery workstation may be remotely located from the radiation treatment system 1200 in a different room than the treatment room in which the radiation treatment system 1200 and patient are located. The treatment delivery workstation 150 may include a processing device (which may be processing device 1230 or another processing device) and memory that modify a treatment delivery to the patient 1225 based on a detection of a target motion that is based on one or more image registrations, as described herein.

Figure 1C:
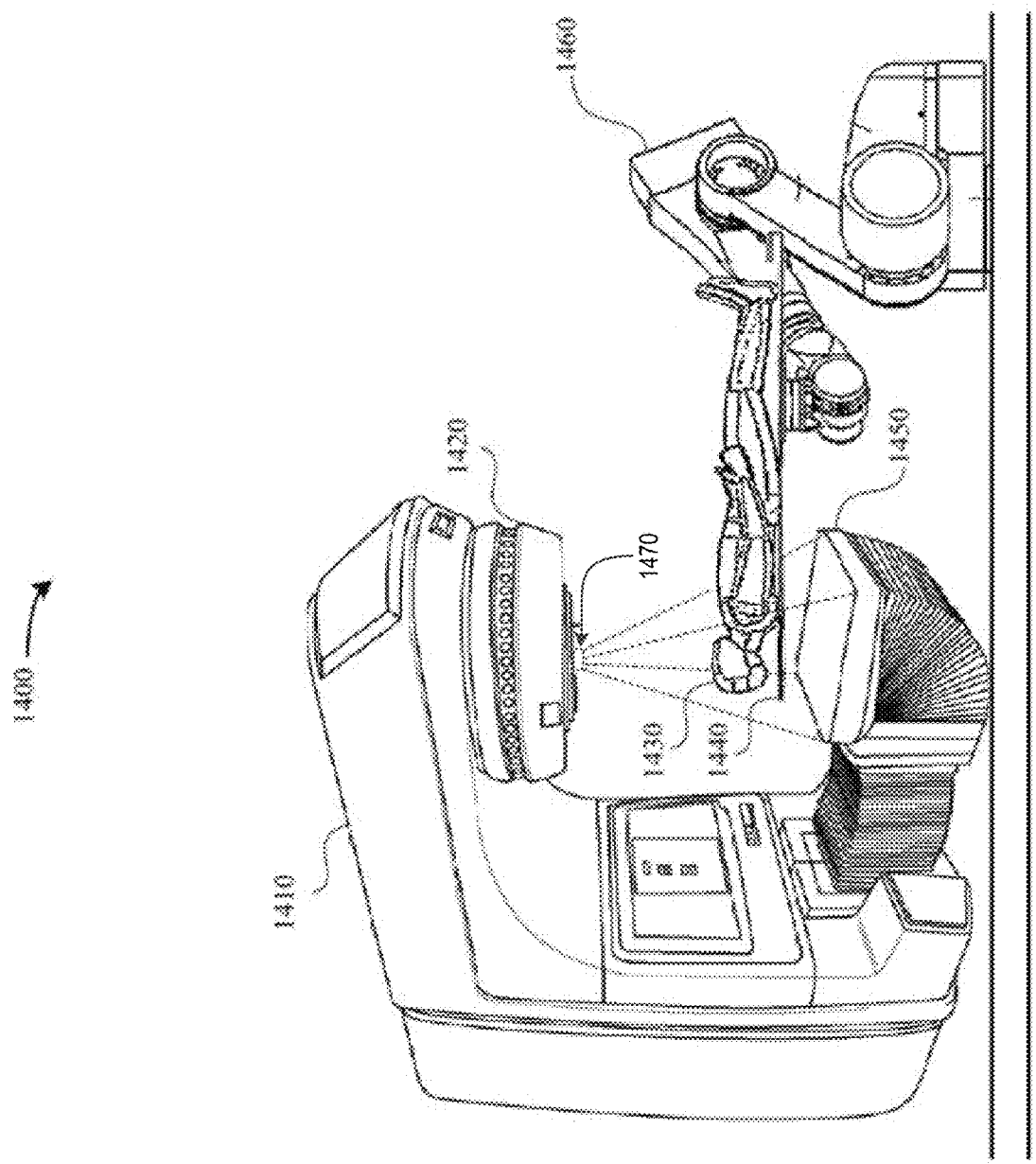
FIG. 1C illustrates a c-arm gantry-based radiation treatment system, in accordance with embodiments described herein.

FIG. 1C. Illustrates a C-arm radiation delivery system 1400. In one embodiment, in the C-arm system 1400 the beam energy of a LINAC may be adjusted during treatment and may allow the LINAC to be used for both x-ray imaging and radiation treatment. In another embodiment, the system 1400 may include an onboard kV imaging system to generate x-ray images and a separate LINAC to generate the higher energy therapeutic radiation beams. The system 1400 includes a gantry 1410, a LINAC 1420, an MLC 1470 (e.g., an eMLC) coupled with the distal end of the LINAC 1420 to shape the beam, and a portal imaging detector 1450. The gantry 1410 may be rotated to an angle corresponding to a selected projection and used to acquire an x-ray image of a VOI of a patient 1430 on a treatment couch 1440. In embodiments that include a portal imaging system, the LINAC 1420 may generate an x-ray beam that passes through the target of the patient 1430 and are incident on the portal imaging detector 1450, creating an x-ray image of the target. After the x-ray image of the target has been generated, the beam energy of the LINAC 1420 may be increased so the LINAC 1420 may generate a radiation beam to treat a target region of the patient 1430. In another embodiment, the kV imaging system may generate an x-ray beam that passes through the target of the patient 1430, creating an x-ray image of the target. In some embodiments, the portal imaging system may acquire portal images during the delivery of a treatment. The portal imaging detector 1450 may measure the exit radiation fluence after the beam passes through the patient 1430. This may enable internal or external fiducials or pieces of anatomy (e.g., a tumor or bone) to be localized within the portal images.

Alternatively, the kV imaging source or portal imager and methods of operations described herein may be used with yet other types of gantry-based systems. In some gantry-based systems, the gantry rotates the kV imaging source and LINAC around an axis passing through the isocenter. Gantry-based systems include ring gantries having generally toroidal shapes in which the patient's body extends through the bore of the ring/toroid, and the kV imaging source and LINAC are mounted on the perimeter of the ring and rotates about the axis passing through the isocenter. Gantry-based systems may further include C-arm gantries, in which the kV imaging source and LINAC are mounted, in a cantilever-like manner, over and rotates about the axis passing through the isocenter. In another embodiment, the kV imaging source and LINAC may be used in a robotic arm-based system, which includes a robotic arm to which the kV imaging source and LINAC are mounted as discussed above. Aspects of the present disclosure may further be used in other such systems such as a gantry-based LINAC system, static imaging systems associated with radiation therapy and radiosurgery, proton therapy systems using an integrated image guidance, interventional radiology and intraoperative x-ray imaging systems, etc.

Figure 2A:
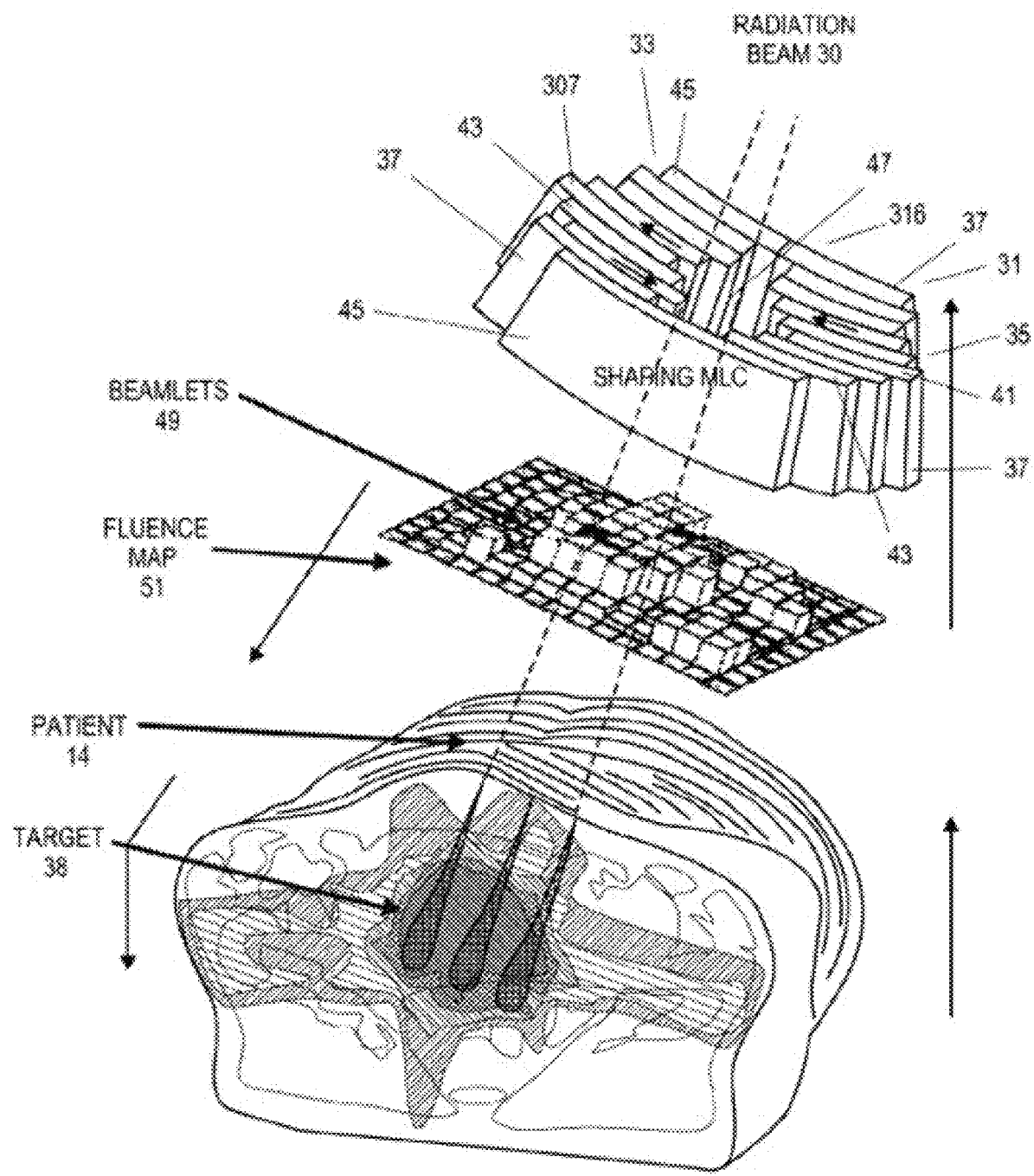
FIG. 2A illustrates a multileaf MLC to provide a radiation treatment dose to a target region, in accordance with embodiments described herein.

FIG. 2A illustrates a multileaf collimator (MLC) 31 to provide a radiation treatment dose to a target region, in accordance with embodiments described herein. MLC 31 includes two banks of opposing leaves 33, where each leaf 37 may be positioned continuously across the radiation field. The two banks of leaves 33 are positioned so as to collimate the beam 30 in the desired shape. In one embodiment, each leaf 37 may travel beyond the midpoint of the collimator in order to provide flexibility when achieving the desired collimation. The configuration illustrates fully open (41), partially open (43) and closed (45) leaf states.

In an example of radiation therapy, each gantry angle has one beam associated with that particular gantry angle, which beam 30 is then collimated into multiple shapes by an MLC. Treatment beam 30 passes through the shaped aperture 47 formed by the leaves 37. The resulting collimated beam continues onto a target 14 within the patient 38. FIG. 2A also illustrates how the treatment beam may be visualized or conceptualized as many different beamlets 49. Leaves 37 of the MLC 31 are moved into various positions to achieve desired shapes or apertures for specified periods of time to achieve fluence map 51 for that particular beam. Modulation of the conceptualized beamlets occurs by sequentially and monotonically moving the leaves into desired positions to achieve desired shapes or apertures such that the time a conceptualized beamlet is exposed controls the intensity of that beamlet. In one embodiment, "monotonic," as herein, means an ordered sequence of apertures where the sequence is dictated by a continuum from one aperture to a subsequent aperture, or where individual leaves increment in one direction during a given series of apertures. In other words, a sequence of apertures would be dictated by mechanical limitations of the MLC, not so much by what may achieve the more optimal treatment delivery. In one embodiment, a sequence would go from aperture 1, then 2 then 3 and so on, and not from 1 to 3 then to 5 then back to 2. Rather than use a single conformal shape, the MLC may deliver a sequence of shapes. The net amount of radiation received at any given gantry position is based upon the extent to which the different shapes permit the passage or blockage of radiation. As seen in FIG. 2A, the shape of MLC 31 shown does not directly correspond to the beamlet intensities of the fluence map 51. As will be appreciated, the depicted fluence map shows the accumulation of intensities for multiple shapes the MLC has taken for that particular gantry angle.

A common limitation of conventional shaping MLCs is that the leaves defining the shapes move relatively slowly. Using a large numbers of shapes, or shapes that require large leaf motions, can result in longer patient treatments. Likewise, the speed of the leaves can limit the ability of conventional shaping-MLC's to deliver time-sensitive treatments, such as utilizing synchronized motion of delivery components (e.g., gantry, couch, x-ray energy etc.). In part for these reasons, prior 2-D intensity map delivery techniques have been limited to beams delivered from static positions. Alternately, prior systems that do allow continuous motion of the radiation source generally only allow single aperture shapes or morphing from one aperture shape to another as the radiation source moves, and do not allowed a 2-D intensity map to be delivered from each radiation source position.

Figure 2B:
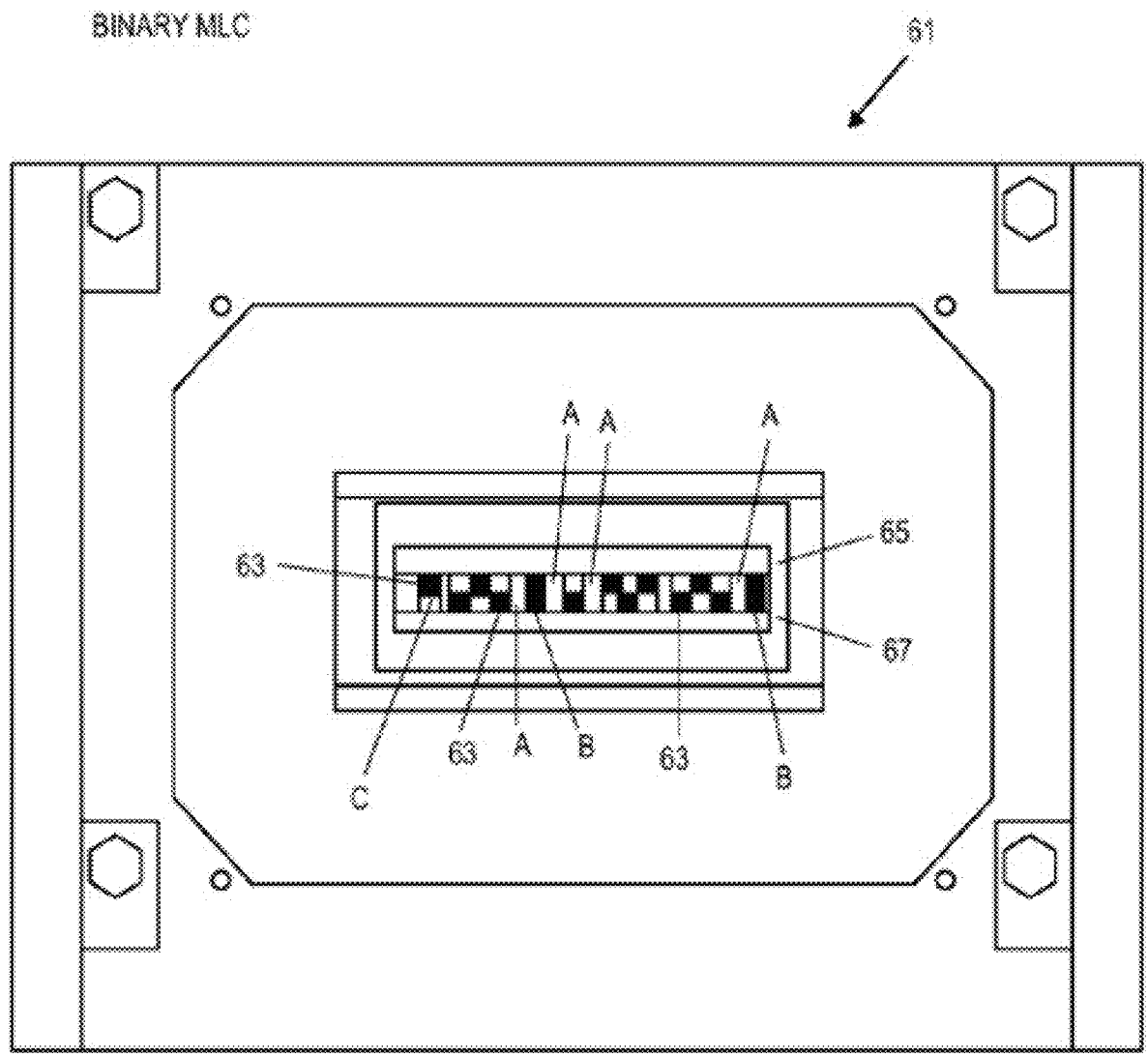
FIG. 2B illustrates a bottom view of a multileaf MLC, in accordance with embodiments described herein.

FIG. 2B illustrates a bottom view of a multileaf MLC 61, in accordance with embodiments described herein. The binary MLC 61 has a plurality of leaves 63 arranged in two banks 65, 67. Each bank of leaves is used to form a treatment slice by positioning the leaf in a closed position or open position with respect to the beam. As shown in FIG. 2B, the leaves may work in concert to be both open (A), both closed (B), or where only one leaf is open/closed (C). In a conventional binary MLC, the leaves 63 open (A) to the same, uniform width during an entire single positional section. In a conventional shaping MLC, the leaves 63 may open (A) to different, various widths during an entire single positional section. A common limitation of conventional binary MLCs is that the leaves 63 may not be open to a variety of different widths for any fraction of time during each positional section. Thus, shaping radiation beams to a target area while simultaneously minimizing radiation exposure to non-target areas may be difficult. Advantageously, the methods and systems described herein, allow for the benefits of a shaping MLC (e.g., the leaves 63 may be open to a variety of different widths for any fraction of time during each positional section), while maintaining the speed of a binary MLC.

Figure 2C:
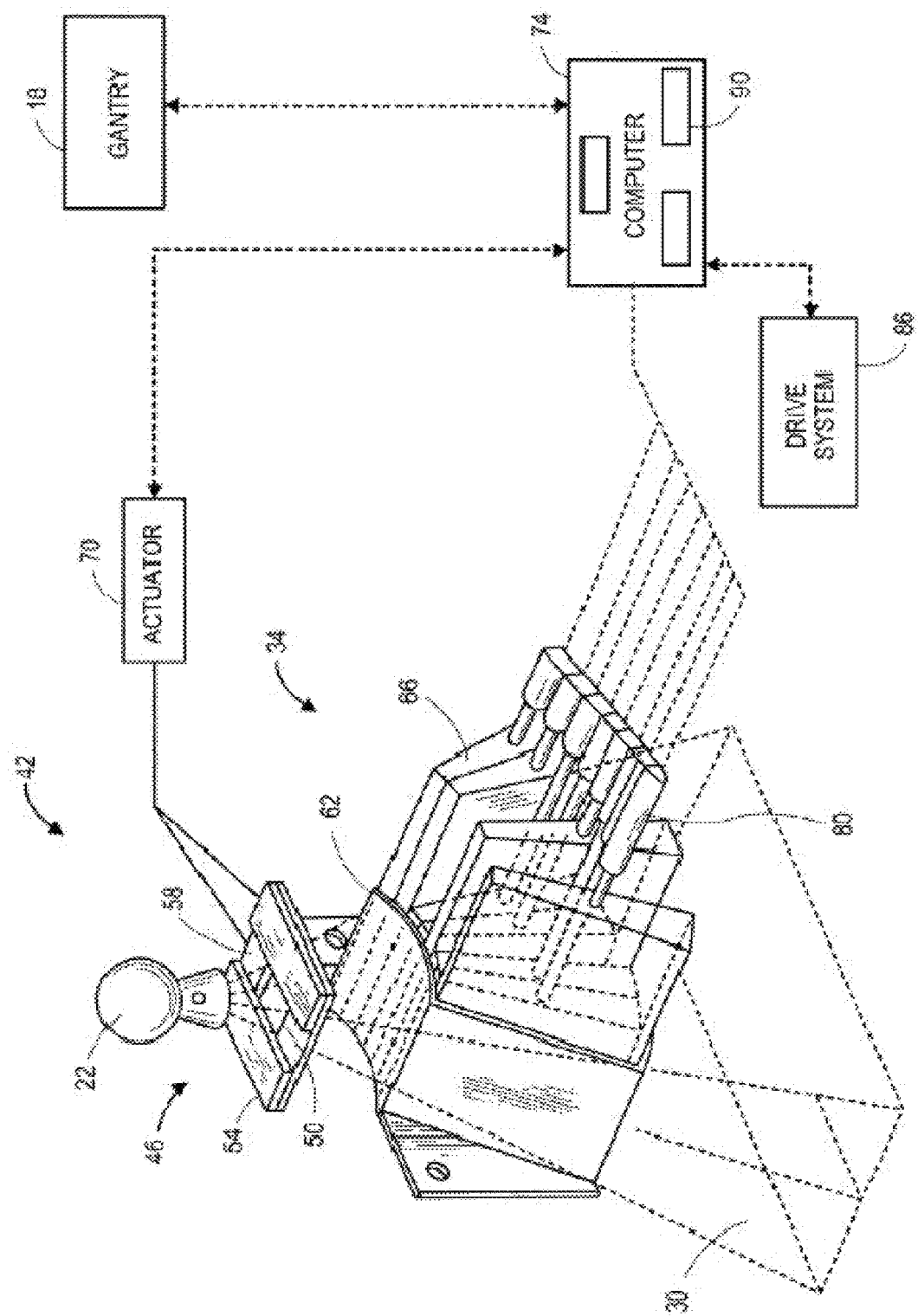
FIG. 2C illustrates a perspective view of a multileaf high-speed MLC, in accordance with embodiments described herein.

FIG. 2C illustrates a perspective view of a multileaf high-speed MLC 62, in accordance with embodiments described herein. In one embodiment, a radiation modulation device 34 includes an electromagnetically actuated MLC (eMLC) 62, which includes a plurality of leaves 66 operable to move from position to position, to provide intensity modulation. Leaves 66 can move to any position between a minimally and maximally-open position, with sufficient speed such that leaf sequencing or positioning will not be significantly influenced by any previous or future positions of any individual leaf Stated another way, leaf speed is sufficient such that the mechanics of the MLC do not unduly influence the determination of leaf position at any given time for the delivery of a radiation therapy treatment or fraction. Each leaf 66 is independently controlled by an actuator (not shown, but more fully described below), such as a motor, or magnetic drive in order that leaves 66 are controllably moved from fully open, fully closed or to any position between open and closed as described in greater detail below. The actuators can be suitably controlled by computer 74 and/or a controller.

In one embodiment, the MLC 62 is coupled with the distal end of the LINAC of a radiation treatment delivery system. A processing device of the computer 74 may control the plurality of leaf pairs 66 of the MLC 62 such that for each of a plurality of radiation beam delivery positional sections corresponding to a range of radiation beam positions over a discrete time interval, each leaf pair of the plurality of opposing leaf pairs 66 is open to a fixed opening for a fraction of time in the discrete time interval and closed for the remaining fraction of time in the discrete time interval, while a radiation beam of the radiation treatment system is active. In one embodiment, the fixed opening and the fraction of time form overlapping radiation fields of different intensities that combine to result in an intensity modulated fluence field delivered to a treatment target. In one embodiment, the fixed opening conforms to the outline of a treatment target, projected back along the radiation beam to the MLC, and within a maximum range of travel of plurality of leaf pairs within the MLC. This concept is further described with respect to FIGS. 4A-C and FIG. 5B.

In one embodiment, the processing device of the computer 74 may control the MLC 62 to modulate a sub-beam intensity of the radiation beam across a plurality of sub-beams that subdivide a fluence field into a 2D grid, and wherein a plurality of independent 2D sub-beam intensity patterns are delivered from a plurality of gantry angles while the gantry moves continuously. This concept is further described with respect to FIGS. 3A-F and FIG. 5A.

In one embodiment, the LINAC including the MLC 62 is mounted on a rotating gantry, wherein radiation beams delivered from the range of radiation beam positions rotate around a treatment target. The treatment target may be moved axially through a bore of the rotating gantry, and the radiation beams delivered from the range of radiation beam positions may follow a helical path about the treatment target. In another embodiment, the LINAC and the MLC 62 are mounted on a robotic arm, and the radiation beam delivered from the range of radiation beam positions is non-coplanar.

Figure 2D:
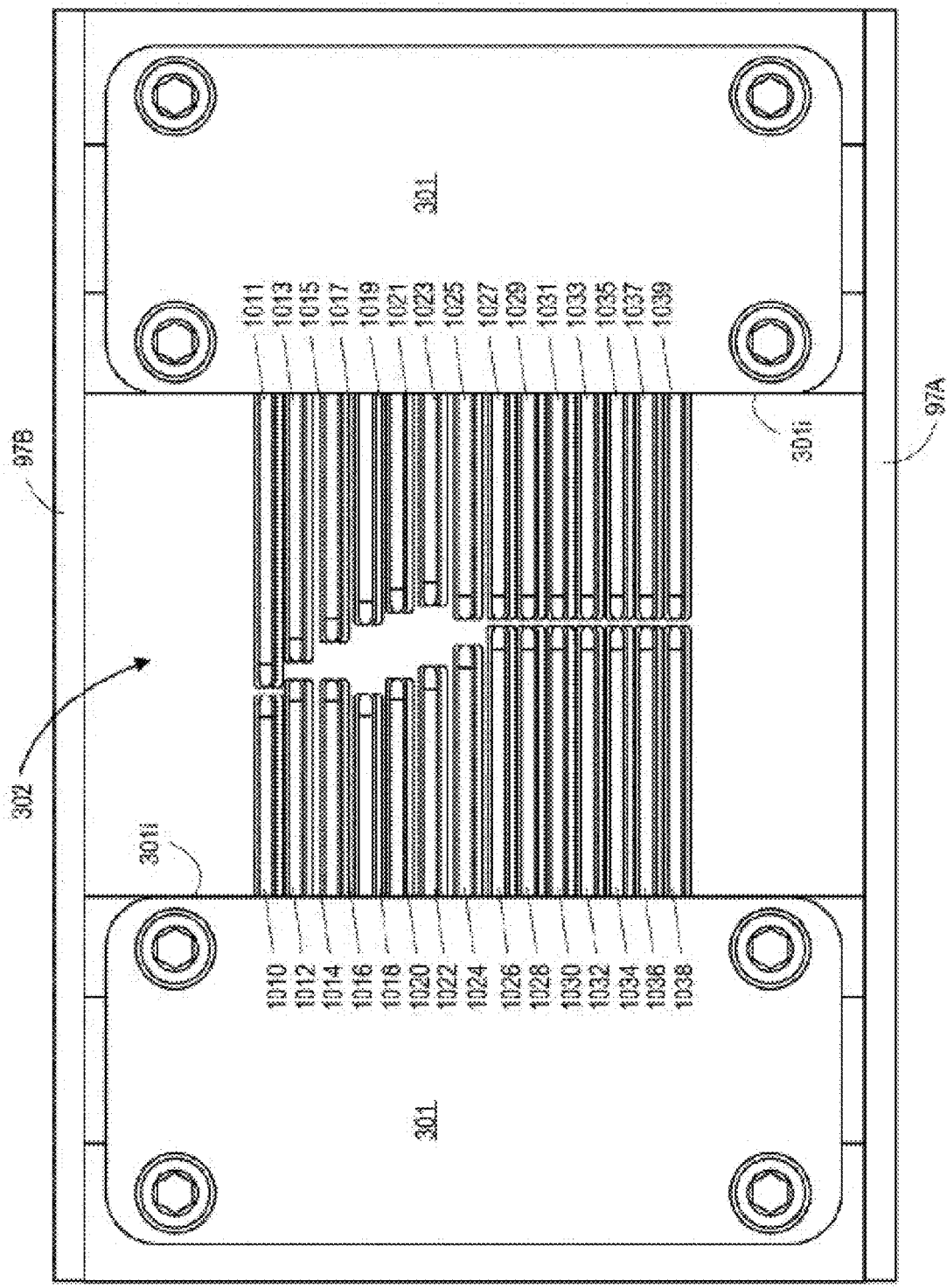
FIG. 2D illustrates a top view of the leaves of a multileaf high-speed MLC, in accordance with embodiments described herein.

FIG. 2D illustrates a top view of the leaves of a multileaf high-speed MLC 240, in accordance with embodiments described herein. Central portion 302 of MLC 240 includes inner leaf guides 301, aperture 1050 and 14 leaf pairs (1010-1039) in various positions between leaf guide inner supports 301. While 14 leaf pairs are shown, more or fewer leaf pairs may be provided according to the design requirements of a particular system. In one embodiment, there are 64 leaf pairs. In another embodiment, there are 96 leaf pairs. In still another embodiment, there are 32 leaf pairs. As will be apparent, radiation is collimated through this section 302 of the collimator.

In FIG. 2D, each leaf is positioned in a particular position to define a particular aperture or shape 1050, through which radiation may pass, also referred to herein as a state. Leaf pairs 1010 and 1011 through 1038 and 1039 are controlled using the control schemes and drivers described herein to enable simultaneous volume and intensity modulation. In alternative aspects, one or more controllable jaws are used to provide primary collimation of the beam, defined by the inner edges 301 *i* and the frames 97A, 97B (i.e., the jaws will block the open space between support frame B and leaf pair 1010/1011 and between support frame A and leaf pair 1038/1039). Additionally or alternatively, the one or more pairs of jaws may be adjusted to reduce the size of the primary collimated beam to smaller than the frame size.

Figure 2E:
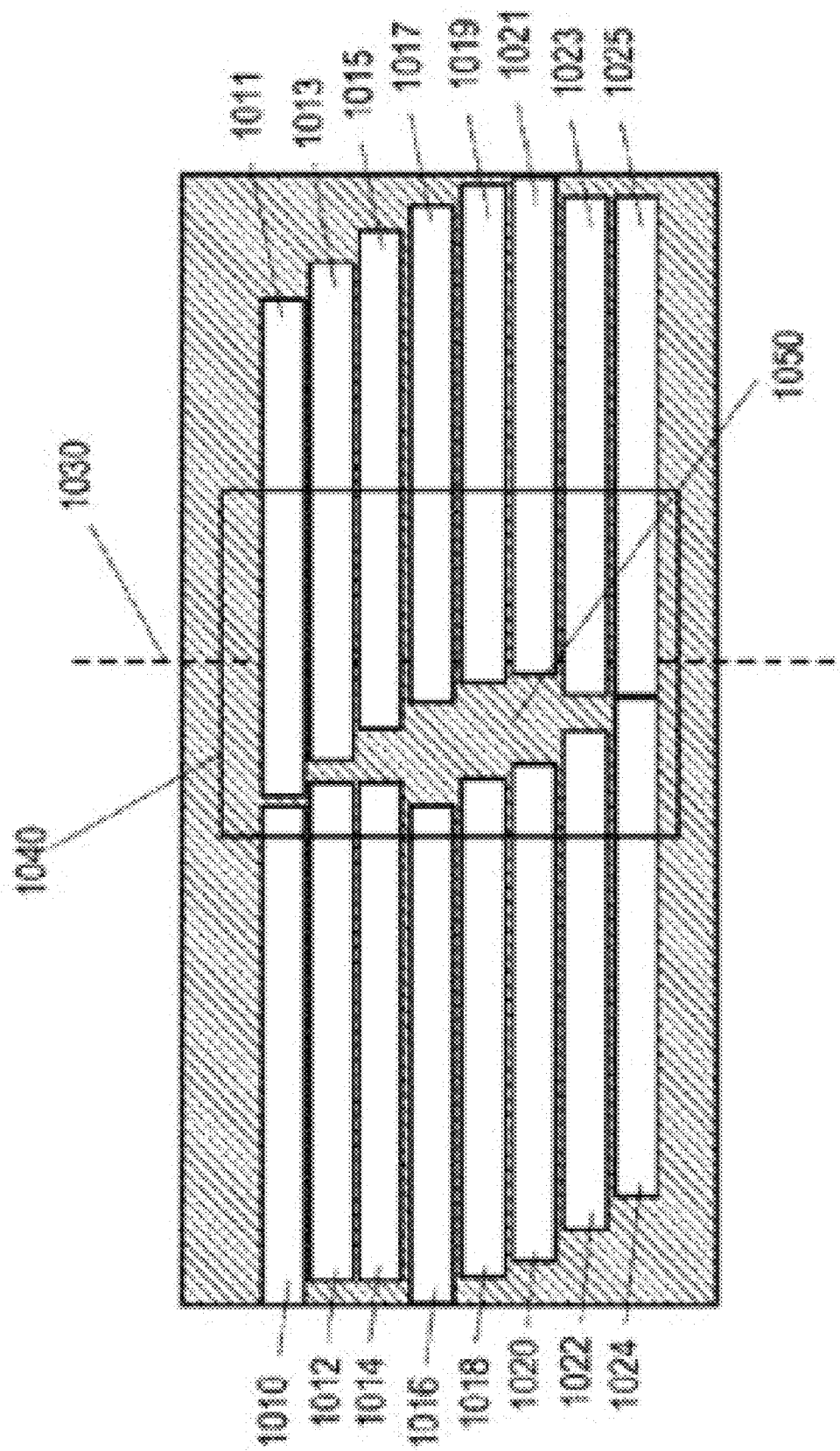
FIG. 2E illustrates an exemplary leaf arrangement for a multileaf high-speed MLC, in accordance with embodiments described herein.

FIG. 2E illustrates an exemplary leaf arrangement for a multileaf high-speed MLC, in accordance with embodiments described herein. A collimated field 1040 having a center line 1030 is provided by a pair of jaws or other collimator device. In the illustrative embodiment, two leaves form a complementary leaf pair for shaping and modulation of the collimated field 1040. For example, leaves 1010 and 1011 are one leaf pair. Leaves 1018, 1019 are another and leaves 1024, 1025 still another. Each leaf in each pair may be positioned anywhere within field 1040. The inner edges of each leaf within a leaf pair face each other and may create an opening, the collection of openings formed by each leaf pair forms aperture 1050. Aperture 1050 corresponds to an aperture of FIG. 2D previously described and is set according to a treatment plan. In one embodiment, an aperture 1050 is determined prior to administering radiation therapy to a patient in the treatment planning process, and occurs at a particular point during delivery of the treatment plan. Aperture 1050 may change according to a number of factors, such as for example, the three dimensional shape of the treatment area, intensity modulation, fluence, and beamlets within a treatment volume, as described herein. Embodiments of the high-speed MLCs described herein achieve volume and intensity modulation alone, or in simultaneous combination by providing snap state control.

Figure 3C:
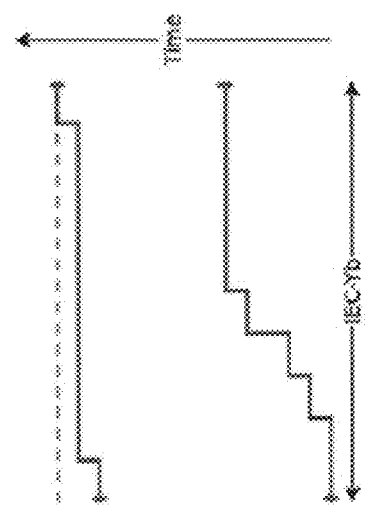
FIGS. 3A-C illustrate exemplary leaf open-time profiles, in accordance with embodiments described herein.
Figure 3F:
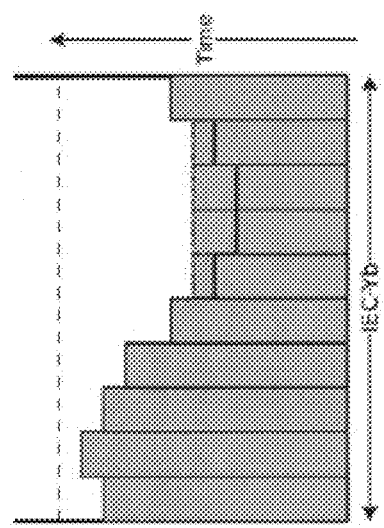
FIGS. 3D-F illustrate exemplary optimized leaf open-time profiles, in accordance with embodiments described herein.
Figure 3B:
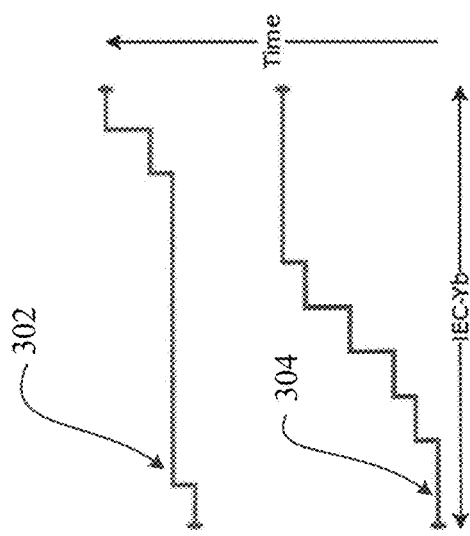
Figure 3E:
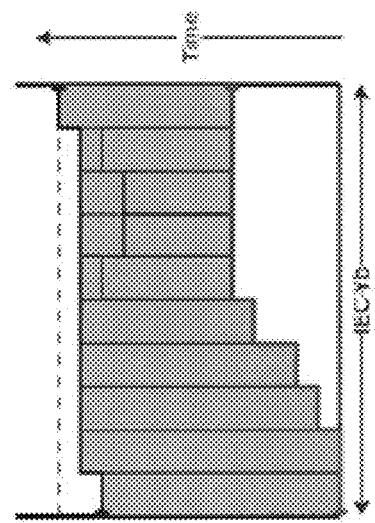
Figure 3A:
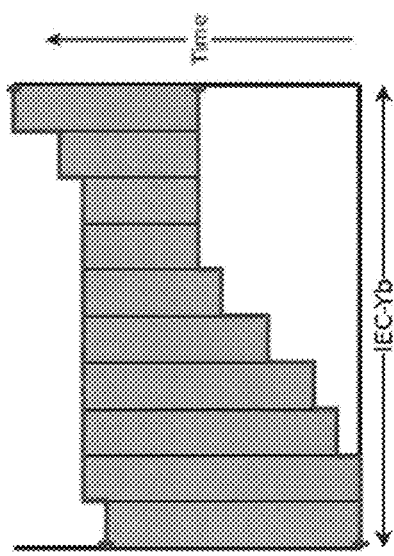

FIGS. 3A-C illustrate exemplary leaf open-time profiles, in accordance with embodiments described herein. Unlike using traditional MLCs, by using an eMLC (or some other suitable high-speed MLC) the amount of fluence transmitted at each point along the leaf-pair's direction of travel (e.g., the IEC-Yb direction) may be precisely controlled, while at the same time the constantly moving radiation source (e.g., the LINAC) traverses an arc short enough to be considered as one position. To generate a plan for such a high-speed MLC, leaf-open-time profiles may be determined. In one embodiment, a leaf-open-time profile indicates the open time for leaf pairs for a discrete time interval.

To generate an eMLC plan, a leaf-open-time profile for each leaf pair in each positional section may be divided into discrete beamlets. An optimizer may determine an ideal leaf-open-time for each beamlet, as described below. From the leaf-open-time profile, front and back leaf-motion profiles for each leaf pair may be generated, only allowing leaves to move in a single direction in each positional section. In one embodiment, leaves alternate between moving back-to-front and front-to-back in successive positional sections, so as a leaf-pair finishes its travel in one positional section it will be in position to begin its travel in the next positional section.

FIG. 3A illustrates an example leaf-open-time profile. As shown, the leaf-pair open-times, represented by the bars sitting on the IEC-Yb axis, may be different for each leaf pair. Note that in the leaf motion profile algorithm described above, the total time needed to deliver all the leaf-pair open-times is:

$$w(1) + \sum_{i=2}^{n} \max\{w(i) - w(i-1), 0\}$$

Or, equivalently:

$$w(n) + \sum_{i=1}^{n-1} \max\{w(i) - w(i+1), 0\}.$$

If this total time is less than the discrete time interval for the positional section, then the leaf motion profiles may be centered in the positional section, as shown in FIG. 3B. FIG. 3C illustrates the leading leaf motion 302 and the trailing leaf motion 304, centered in the positional section.

Figure 3D:
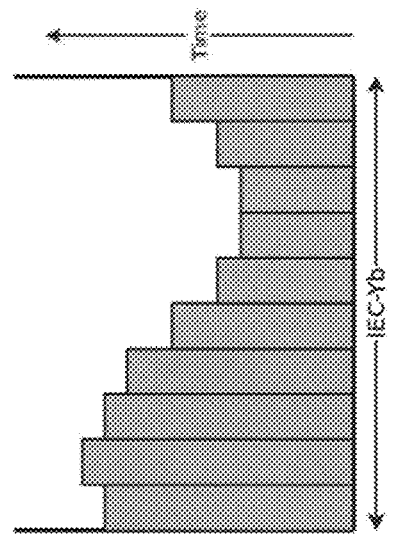

FIGS. 3D-F illustrate exemplary optimized leaf open-time profiles, in accordance with embodiments described herein. In one embodiment, a modulation factor constraint may be applied to the leaf-open-time profiles so that the leaf open times are not excessively large (and thus delay treatment time). To generate the modulation factors, the average beamlet open-time is calculated for all non-zero beamlets across all leaves and positional sections. The discrete time interval is then determined to be the average open-time, multiplied by the desired modulation factor. For each positional section and leaf; beamlet open-times are then adjusted such that the total leaf-open time is no greater than the discrete time interval corresponding to the positional section.

There are several ways to make this adjustment. In one embodiment, individual beamlet open-times that are greater than the discrete time interval may be decreased to be equal to the projection time, and then the smallest beamlet open-times may be increased until the total leaf open-time is less than or equal to the discrete time interval, as illustrated in FIGS. 3D-F.

Figure 3G:
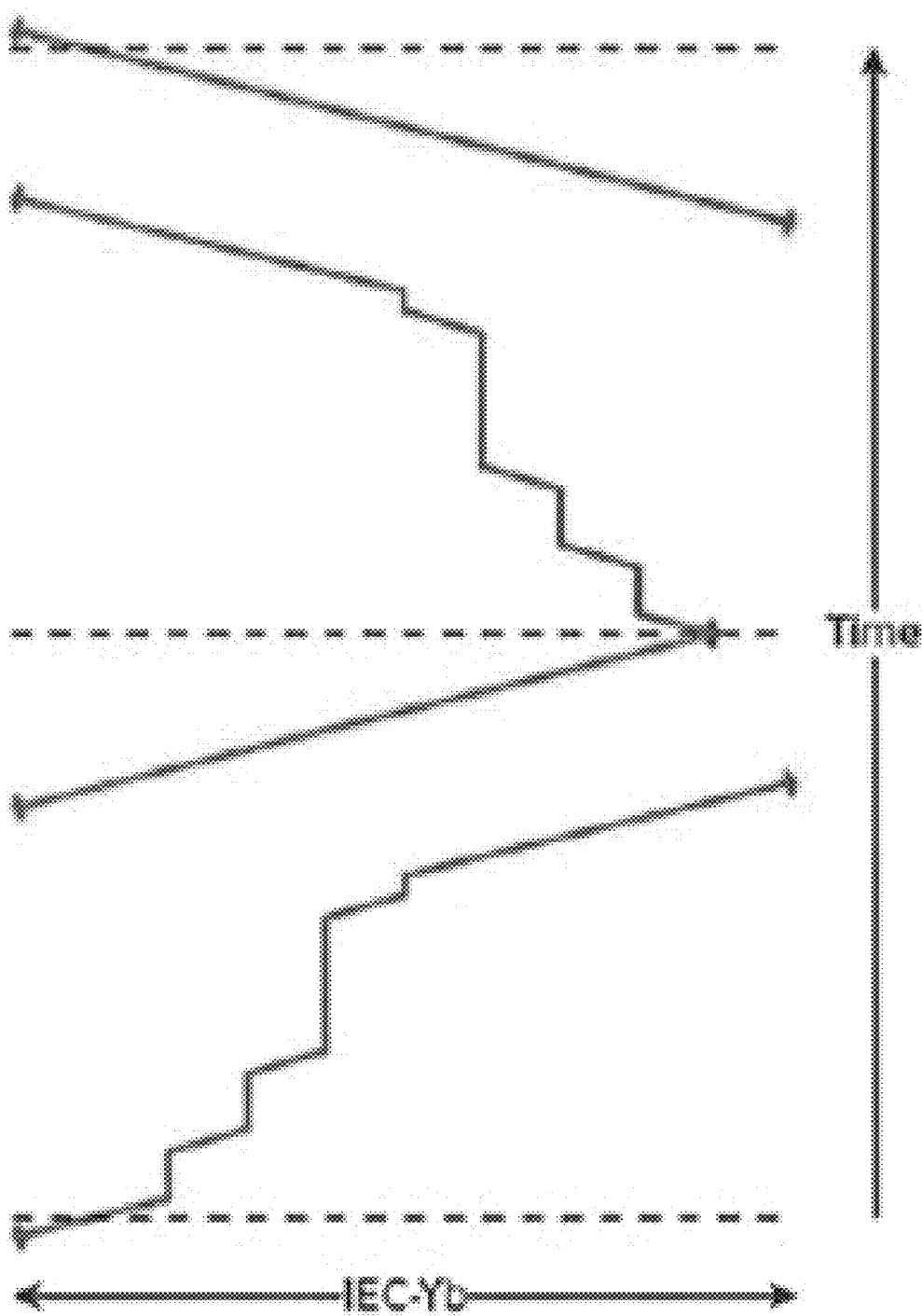
FIG. 3G illustrates an exemplary leaf open-time profile that incorporates a maximum velocity, in accordance with embodiments described herein.

FIG. 3G illustrates an exemplary leaf open-time profile that incorporates a maximum velocity, in accordance with embodiments described herein. Notably, the leaves of a high-speed MLC move quickly, but not instantaneously. To generate a plan that is actually deliverable, leaf motion profiles may account for the finite leaf speed of the MLC. In one embodiment, this can be done by incorporating a maximum leaf velocity (and possibly leaf acceleration) into the generated leaf profiles. In one embodiment, the algorithm may strive to keep the area in each column constant. In the example profile 306, instantaneous leaf motion has been changed to leaf motion with a finite velocity. Note that the leaf motion in each segment may begin a little early, so that the integral open time for the beamlets remains unaffected. In one embodiment, if the start of travel in the next projection overlaps with the end of travel in the current projection, then the leaf may change direction before reaching the end of its travel, resulting in slightly less fluence being delivered to the target area. The operations of FIGS. 3A-G are described further with respect to FIG. 5A.

Figure 4A:
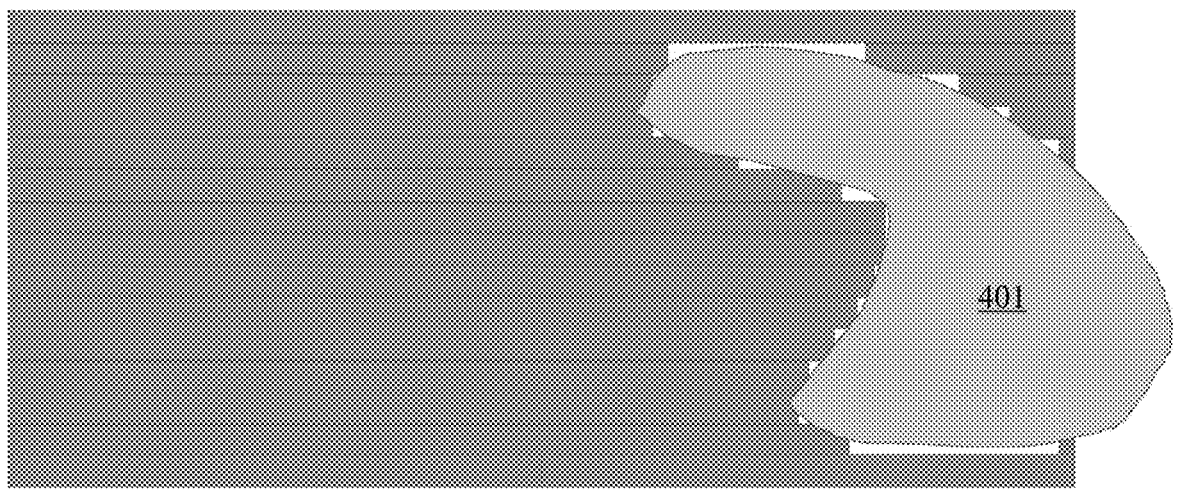
FIGS. 4A-C illustrate a variety of exemplary leaf arrangements conforming to a target region, in accordance with embodiments described herein.
Figure 4B:
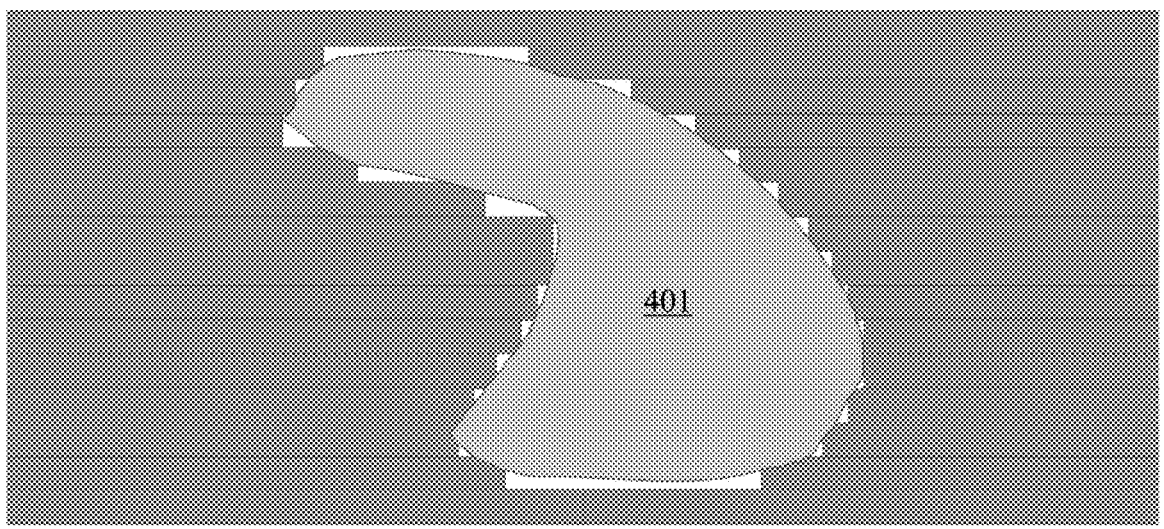
Figure 4C:
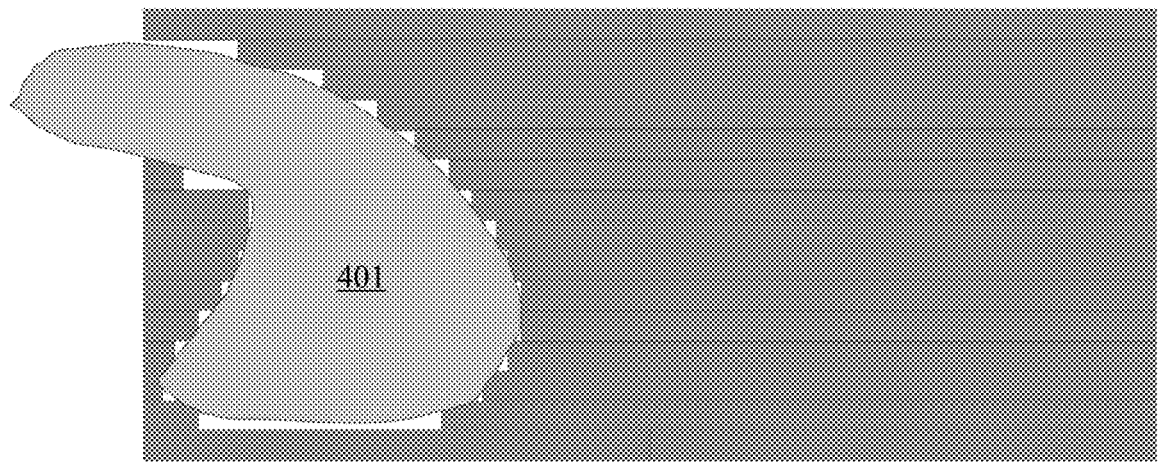

FIGS. 4A-C illustrate a variety of exemplary leaf arrangements conforming to a target region 401, in accordance with embodiments described herein. Each leaf pair is positioned in a particular way such that the leaf pair openings define a particular aperture or shape to conform to target region 401. During treatment, radiation passes through the aperture defined by the combined leaf pairs, and strikes the target region below. A high-speed MLC (e.g., an eMLC), such as that described herein, opens and closes each leaf pair to an open state or a closed state during a discrete time interval. Each leaf pair may be open for a different fiction of time (e.g., an open-time fraction) during the discrete time interval, and each leaf pair may be open to a different width during a corresponding open-time fraction. Furthermore, the treatment beam may be active during the entire discrete time interval.

Advantageously, by activating the treatment beam during the entire discrete time interval, and allowing each leaf pair to be open for only a fraction of the discrete time interval to a specified width (which may be different than widths of other leaf pairs), precise doses of radiation may be delivered to a variety of complicated target region shapes. The operations of FIGS. 4A-C are described further with respect to FIG. 5B.

Figure 5A:
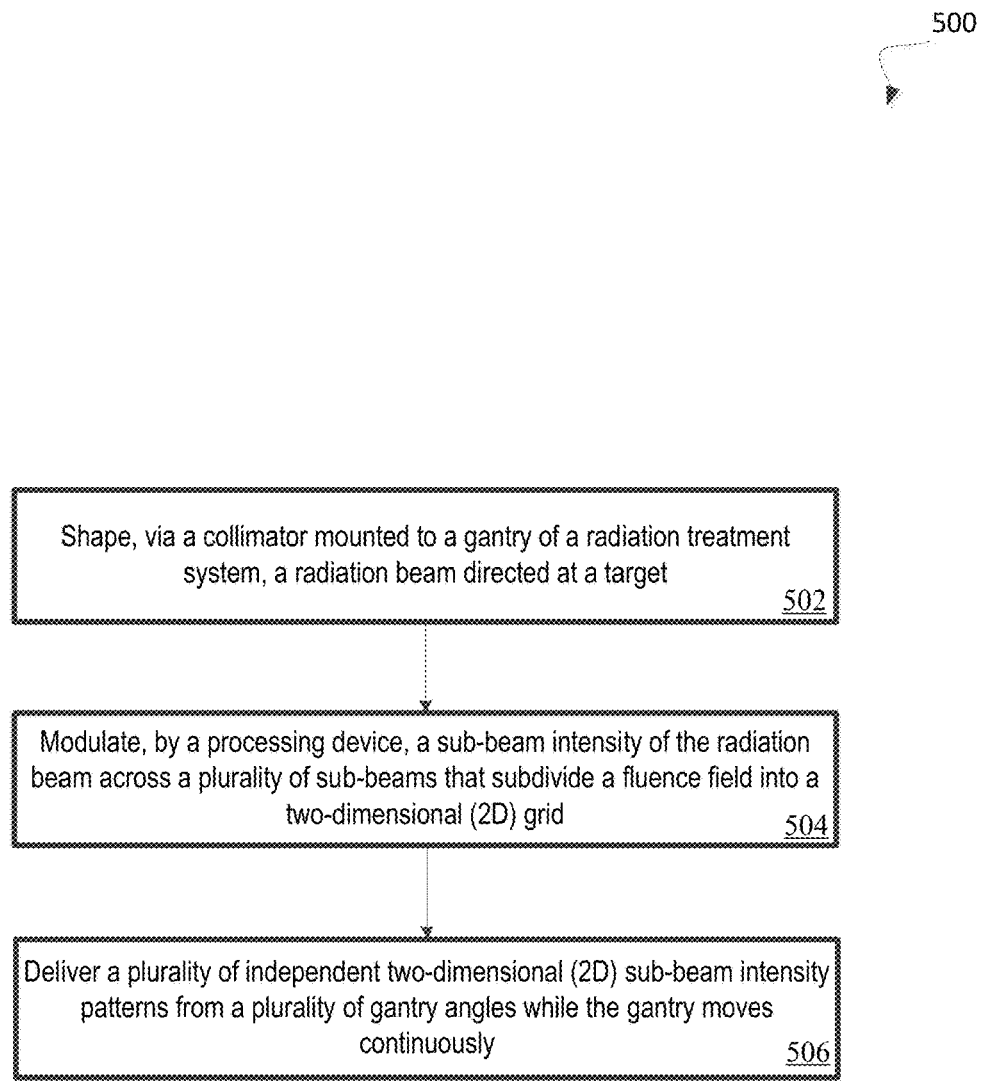
FIG. 5A is a flowchart illustrating a method for fast sliding window with a high-speed MLC, in accordance with embodiments described herein.

FIG. 5A is a flowchart illustrating a method 500 for fast sliding window with a high-speed MLC, in accordance with embodiments described herein. In general, the method 500 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 500 may be performed by processing logic of the radiation treatment system 800 of FIG. 1A.

As shown in FIG. 5A, the method 500 may begin at block 502 with the processing logic shaping, via a collimator mounted to a gantry of a radiation treatment system, a radiation beam directed at a target. In one embodiment, the collimator is a multileaf collimator (MLC) comprising a plurality of leaf pairs. The MLC may be a high-speed MLC (e.g., an eMLC), as described herein.

Processing logic at block 504 may modulate, by a processing device, a sub-beam intensity of the radiation beam across a plurality of sub-beams that subdivide a fluence field into a 2D grid. In one embodiment, the sub-beam intensity is modulated by independently modulating a rate of travel of front and back leaves in each leaf pair, as each leaf pair moves in a single pass from one end of a corresponding line of travel to another end of the corresponding line or travel. Additional details corresponding to the modulation of sub-beam intensities are provided with respect to FIGS. 3A-G.

In a variety of embodiments, the 2D grid described herein is a rectangular grid. In other embodiments, the 2D grid is any shape. In one embodiment, a first axis of the 2D sub-beam grid is determined by an index of the leaf pairs along one axis of the MLC, and a second axis of the 2D grid is along a line of travel of the leaf pairs.

Processing logic at block 506 may deliver a plurality of independent 2D sub-beam intensity patterns from a plurality of gantry angles. In one embodiment, the plurality of independent 2D sub-beam intensity patterns may be delivered from a plurality of gantry angles while the gantry moves continuously. In one embodiment, each of the plurality of leaf pairs changes direction when delivering the fluence pattern for each subsequent gantry angle.

In one embodiment, processing logic may constrain the motion of the plurality of leaf pairs used to deliver the 2D fluence pattern from a particular gantry angle to occur in less than a pre-selected time period (as described with respect to FIG. 3D-F). In one embodiment, processing logic may center leaf pair motion for a particular gantry angle that takes less than the pre-selected time period within the pre-selected time period (as described with respect to FIG. 3A-F). In one embodiment, a first leaf in a leaf pair that follows a second leaf in the leaf pair when delivering the intensity pattern from a particular gantry angle does not reach the end of its travel before reversing direction to deliver the intensity pattern for a subsequent gantry angle (e.g., leaf pairs to not need to wait for other leaf pairs to end their travel before reversing direction).

In one embodiment, the continuous motion of the gantry may be a helical motion. For example, processing logic may rotate the gantry continuously, wherein the 2D sub-beam intensity pattern for a particular gantry angle is approximated by delivering the intensity pattern over a small arc. As used herein, "small arc" may refer to a sub-arc of the total gantry rotation that is small enough that it may be treated as a single gantry angle for the purposes of planning the intended dose distribution. In one embodiment, "small arc" may refer to approximately 7 degrees around the total gantry rotation. In other embodiments, other arc sizes may be used to deliver one-dimensional beamlet intensity patterns.

In one embodiment, processing logic moves the target axially through a center of the gantry via an axial support (e.g., a treatment couch), wherein the gantry and axial support move simultaneously during irradiation of the target to perform a helical delivery. In one embodiment, the helical pitch during the irradiation of the target is greater than or equal to 0.5. In other embodiments, other helical pitches greater than or less than 0.5 may be used.

Figure 5B:
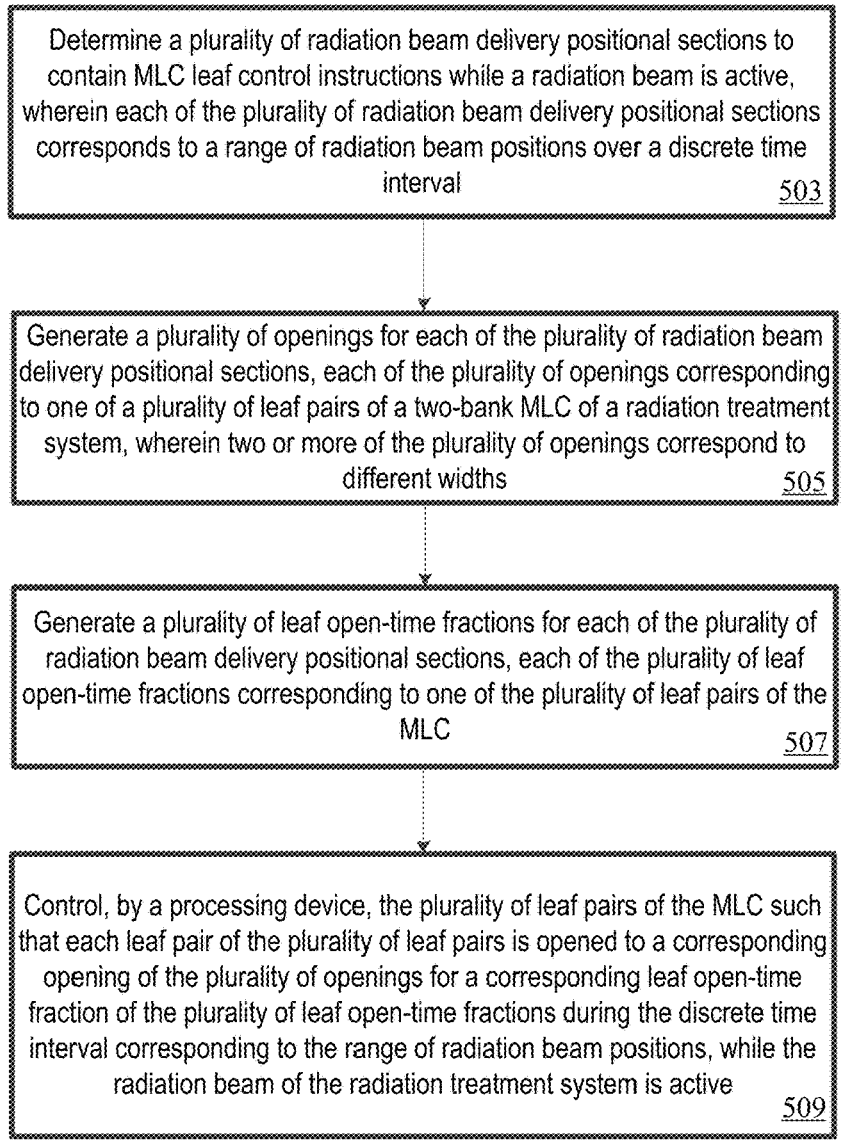
FIG. 5B is a flowchart illustrating a method for binary MLC delivery with a per-leaf field width, according to embodiments.

FIG. 5B is a flowchart illustrating a method 501 for binary MLC delivery with a per-leaf field width, according to embodiments. In general, the method 501 may be performed by processing logic that may include hardware (e.g., processing device, circuitry, dedicated logic, programmable logic, microcode, hardware of a device, etc.), software (e.g., instructions run or executed on a processing device), or a combination thereof. In some embodiments, the method 501 may be performed by processing logic of the radiation treatment system 800 of FIG. 1A.

As shown in FIG. 5B, the method 501 may begin at block 503 with the processing logic determining a plurality of radiation beam delivery positional sections to contain MLC leaf control instructions while a radiation beam is active. In one embodiment, as described herein, each of the plurality of radiation beam delivery positional sections corresponds to a range of radiation beam positions over a discrete time interval (e.g., along an arc of a gantry of the radiation treatment system). For example, the radiation beam delivery positional sections (e.g., projections) may correspond to the radiation beam being delivered from at least one of a different position or a different direction.

In other words, the positional sections may be thought of as positional nodes, from which a LINAC may deliver a radiation treatment beam in a particular direction. The positional sections may include a range of positions (e.g. a zone). For example, an arc in a helical treatment delivery system may be divided into a plurality of discrete positional sections (e.g., where each positional section includes some number of degrees around the arc). In one embodiment, a positional section may include approximately seven degrees around an arc (e.g., seven degrees of gantry rotation). In other, non-helical embodiments, positional sections may be defined in terms of three-dimensional spaces. In one embodiment, the different direction remains constant while the different position follows a linear trajectory that sweeps the radiation beam over a length of a treatment target. In one embodiment, the different directions are non-coplanar.

At block 505, processing logic generates a plurality of openings for each of the plurality of radiation beam delivery positional sections, each of the plurality of openings corresponding to one of a plurality of leaf pairs of the MLC.

Advantageously, each of the plurality of openings for each of the plurality of positional sections may correspond to a different width. For example, in one embodiment, two or more of the plurality of openings correspond to different widths in the same positional section. In one embodiment, the plurality of openings conform to an outline of a treatment target, projected back along the radiation beam to the MLC, and within a maximum range of travel of the plurality of leaf pairs within the MLC.

At block 507, processing logic generates a plurality of leaf open-time fractions for each of the plurality of radiation beam delivery positional sections, each of the plurality of leaf open-time fractions corresponding to one of the plurality of leaf pairs of the MLC. In one embodiment, leaf open-time fractions are discrete amounts of time that are less than the discrete time interval. In another embodiment, a leaf open-time fraction may be a discrete amount of time that is equal to the discrete time interval. Advantageously, leaf open-time fractions allow each of the plurality of leaf pairs to be open for a different amount of time during the discrete time interval. For example, in the present embodiment, two or more of the plurality of leaf open-time fractions during the discrete time interval may be different.

At block 509, processing logic controls, by a processing device, the plurality of leaf pairs of the MLC such that each leaf pair of the plurality of leaf pairs is opened to a corresponding opening of the plurality of openings for a corresponding leaf open-time fraction of the plurality of leaf open-time fractions during the discrete time interval corresponding to the range of radiation beam positions, while the radiation beam of the radiation treatment system is active. In one embodiment, the treatment beam is active during the entire discrete time interval (e.g., as the LINAC travels through the positional section).

In one embodiment, the plurality of leaf open-time fractions form overlapping radiation fields of different intensities that combine to result in an intensity modulated fluence field delivered to a treatment target. Advantageously, the above operations allow a radiation treatment delivery system to effectively time-modulate a radiation treatment beam while precisely conforming to the outline of a target area.

Figure 6:
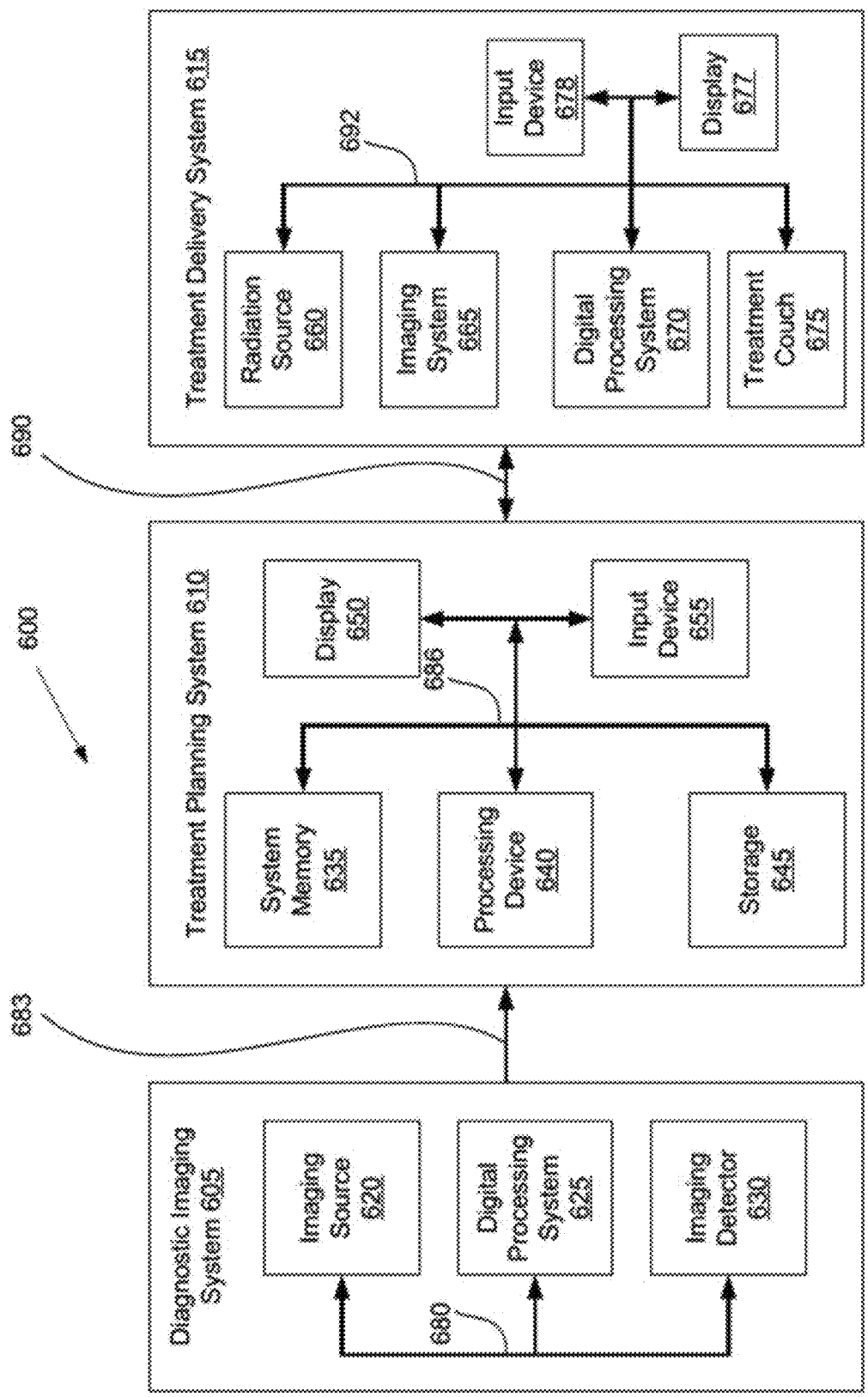
FIG. 6 illustrates examples of different systems that may be used in the generating of the performing of radiation treatment, in accordance with embodiments described herein.

FIG. 6 illustrates examples of different systems 600 within which a set of instructions, for causing the systems to perform any one or more of the methodologies discussed herein, may be executed. In alternative implementations, the machine may be connected (e.g., networked) to other machines in a LAN, an intranet, an extranet, and/or the Internet. Each of the systems may operate in the capacity of a server or a client machine in client-server network environment, as a peer machine in a peer-to-peer (or distributed) network environment, or as a server or a client machine in a cloud computing infrastructure or environment.

The systems are machines capable of executing a set of instructions (sequential or otherwise) that specify actions to be taken by that machine. Further, while a single machine is illustrated, the term "machine" shall also be taken to include any collection of machines that individually or jointly execute a set (or multiple sets) of instructions to perform any one or more of the methodologies discussed herein.

As described below and illustrated in FIG. 6, a system 600 may include a diagnostic imaging system 605, a treatment planning system 610, and a treatment delivery system 615. Diagnostic imaging system 605 may be any system capable of producing medical diagnostic images of a patient that may be used for subsequent medical diagnosis, treatment planning, treatment simulation and/or treatment delivery. For example, diagnostic imaging system 605 may be a computed tomography (CT) system, a magnetic resonance imaging (MRI) system, a positron emission tomography (PET) system, a combination of such systems, or the like. For ease of discussion, diagnostic imaging system 605 may be discussed below at times in relation to an x-ray imaging modality. In other embodiments, other imaging modalities such as those discussed above may also be used.

In one embodiment, diagnostic imaging system 605 includes an imaging source 620 to generate an imaging beam (e.g., x-rays) and an imaging detector 630 to detect and receive the beam generated by imaging source 620, or a secondary beam or emission stimulated by the beam from the imaging source (e.g., in an MRI or PET scan).

In one embodiment, imaging source 620 and imaging detector 630 may be coupled to a digital processing system 625 to control the imaging operation and process image data. In one embodiment, diagnostic imaging system 605 may receive imaging commands from treatment delivery system 615 and/or treatment planning system 610.

Diagnostic imaging system 605 includes a bus or other means 680 for transferring data and commands among digital processing system 625, imaging source 620 and imaging detector 630. Digital processing system 625 may include one or more general-purpose processors (e.g., a microprocessor), special purpose processor such as a digital signal processor (DSP) or other type of processing device such as a controller or field programmable gate array (FPGA). Digital processing system 625 may also include other components (not shown) such as memory, storage devices, network adapters and the like. Digital processing system 625 may be configured to generate digital diagnostic images in a standard format, such as the Digital Imaging and Communications in Medicine (DICOM) format, for example. In other embodiments, digital processing system 625 may generate other standard or non-standard digital image formats. Digital processing system 625 may transmit diagnostic image files (e.g., the aforementioned DICOM formatted files) to treatment delivery system 615 over a data link 683, which may be, for example, a direct link, a local area network (LAN) link or a wide area network (WAN) link such as the Internet. In addition, the information transferred between systems may either be pulled or pushed across the communication medium connecting the systems, such as in a remote diagnosis or treatment planning configuration. In remote diagnosis or treatment planning, a user may utilize embodiments of the present disclosure to diagnose or treat a patient despite the existence of a physical separation between the system user and the patient.

In one embodiment, treatment delivery system 615 includes a therapeutic and/or surgical radiation source 660 to administer a prescribed radiation dose to a target volume in conformance with a treatment plan. Treatment delivery system 615 may also include imaging system 665 to perform computed tomography (CT) such as cone beam CT, and images generated by imaging system 665 may be two-dimensional (2D) or three-dimensional (3D).

Treatment delivery system 615 may also include a digital processing system 670 to control radiation source 660, receive and process data from diagnostic imaging system 605 and/or treatment planning system 610, and control a patient support device such as a treatment couch 675. Digital processing system 670 may be connected to or a part of a camera feedback system. Digital processing system 670 may be configured to perform any of the operations described herein. Digital processing system 670 may include a processing device that represents one or more general-purpose processors (e.g., a microprocessor), special purpose processor such as a digital signal processor (DSP) or other type of device such as a controller or field programmable gate array (FPGA). The processing device of digital processing system 670 may be configured to execute instructions to perform the operations described herein.

In one embodiment, digital processing system 670 includes system memory that may include a random access memory (RAM), or other dynamic storage devices, coupled to a processing device, for storing information and instructions to be executed by the processing device. The system memory also may be used for storing temporary variables or other intermediate information during execution of instructions by the processing device. The system memory may also include a read only memory (ROM) and/or other static storage device for storing static information and instructions for the processing device.

Digital processing system 670 may also include a storage device, representing one or more storage devices (e.g., a magnetic disk drive or optical disk drive) for storing information and instructions. The storage device may be used for storing instructions for performing the treatment delivery steps discussed herein. Digital processing system 670 may be coupled to radiation source 660 and treatment couch 675 by a bus 692 or other type of control and communication interface.

In one embodiment, the treatment delivery system 615 includes an input device 678 and a display 677 connected with digital processing system 670 via bus 692. The display 677 can show trend data that identifies a rate of target movement (e.g., a rate of movement of a target volume that is under treatment). The display can also show a current radiation exposure of a patient and a projected radiation exposure for the patient. The input device 678 can enable a clinician to adjust parameters of a treatment delivery plan during treatment.

Treatment planning system 610 includes a processing device 640 to generate and modify treatment plans and/or simulation plans. Processing device 640 may represent one or more general-purpose processors (e.g., a microprocessor), special purpose processor such as a digital signal processor (DSP) or other type of device such as a controller or field programmable gate array (FPGA). Processing device 640 may be configured to execute instructions for performing simulation generating operations and/or treatment planning operations discussed herein.

Treatment planning system 610 may also include system memory 635 that may include a random access memory (RAM), or other dynamic storage devices, coupled to processing device 640 by bus 686, for storing information and instructions to be executed by processing device 640. System memory 635 also may be used for storing temporary variables or other intermediate information during execution of instructions by processing device 640. System memory 635 may also include a read only memory (ROM) and/or other static storage device coupled to bus 686 for storing static information and instructions for processing device 640.

Treatment planning system 610 may also include storage device 645, representing one or more storage devices (e.g., a magnetic disk drive or optical disk drive) coupled to bus 686 for storing information and instructions. Storage device 645 may be used for storing instructions for performing the treatment planning steps discussed herein.

Processing device 640 may also be coupled to a display device 650, such as a cathode ray tube (CRT) or liquid crystal display (LCD), for displaying information (e.g., a 2D or 3D representation of the VOI) to the user. An input device 655, such as a keyboard, may be coupled to processing device 640 for communicating information and/or command selections to processing device 640. One or more other user input devices (e.g., a mouse, a trackball or cursor direction keys) may also be used to communicate directional information, to select commands for processing device 640 and to control cursor movements on display 650.

Treatment planning system 610 may share its database (e.g., data stored in storage 645) with a treatment delivery system, such as treatment delivery system 615, so that it may not be necessary to export from the treatment planning system prior to treatment delivery. Treatment planning system 610 may be linked to treatment delivery system 615 via a data link 690, which in one embodiment may be a direct link, a LAN link or a WAN link.

It should be noted that when data links 683, 686, and 690 are implemented as LAN or WAN connections, any of diagnostic imaging system 605, treatment planning system 610 and/or treatment delivery system 615 may be in decentralized locations such that the systems may be physically remote from each other. Alternatively, any of diagnostic imaging system 605, treatment planning system 610, and/or treatment delivery system 615 may be integrated with each other in one or more systems.

It will be apparent from the foregoing description that aspects of the present disclosure may be embodied, at least in part, in software. That is, the techniques may be carried out in a computer system or other data processing system in response to a processing device 625, 640, or 670 (see FIG. 6), for example, executing sequences of instructions contained in a memory. In various implementations, hardware circuitry may be used in combination with software instructions to implement the present disclosure. Thus, the techniques are not limited to any specific combination of hardware circuitry and software or to any particular source for the instructions executed by the data processing system. In addition, throughout this description, various functions and operations may be described as being performed by or caused by software code to simplify description. However, those skilled in the art will recognize what is meant by such expressions is that the functions result from execution of the code by processing device 625, 640, or 670.

A machine-readable medium can be used to store software and data which when executed by a general purpose or special purpose data processing system causes the system to perform various methods of the present disclosure. This executable software and data may be stored in various places including, for example, system memory and storage or any other device that is capable of storing at least one of software programs or data. Thus, a machine-readable medium includes any mechanism that provides (i.e., stores) information in a form accessible by a machine (e.g., a computer, network device, personal digital assistant, manufacturing tool, any device with a set of one or more processors, etc.). For example, a machine-readable medium includes recordable/non-recordable media such as read only memory (ROM), random access memory (RAM), magnetic disk storage media, optical storage media, flash memory devices, etc. The machine-readable medium may be a non-transitory computer readable storage medium.

Unless stated otherwise as apparent from the foregoing discussion, it will be appreciated that terms such as "receiving," "positioning," "performing," "emitting," "causing," or the like may refer to the actions and processes of a computer system, or similar electronic computing device, that manipulates and transforms data represented as physical (e.g., electronic) quantities within the computer system's registers and memories into other data similarly represented as physical within the computer system memories or registers or other such information storage or display devices. Implementations of the methods described herein may be implemented using computer software. If written in a programming language conforming to a recognized standard, sequences of instructions designed to implement the methods can be compiled for execution on a variety of hardware platforms and for interface to a variety of operating systems. In addition, implementations of the present disclosure are not described with reference to any particular programming language. It will be appreciated that a variety of programming languages may be used to implement implementations of the present disclosure.

It should be noted that the methods and apparatus described herein are not limited to use only with medical diagnostic imaging and treatment. In alternative implementations, the methods and apparatus herein may be used in applications outside of the medical technology field, such as industrial imaging and non-destructive testing of materials. In such applications, for example, "treatment" may refer generally to the effectuation of an operation controlled by the treatment planning system, such as the application of a beam (e.g., radiation, acoustic, etc.) and "target" may refer to a non-anatomical object or area.

In the foregoing specification, the disclosure has been described with reference to specific exemplary implementations thereof. It will, however, be evident that various modifications and changes may be made thereto without departing from the broader spirit and scope of the disclosure as set forth in the appended claims. The specification and drawings are, accordingly, to be regarded in an illustrative sense rather than a restrictive sense.

What is claimed is:

1. A method of controlling a two-bank multileaf collimator (MLC) of a radiation treatment delivery system, comprising:
    determining a plurality of radiation beam delivery positional sections to contain MLC leaf control instructions while a radiation beam is active, wherein each of the plurality of radiation beam delivery positional sections corresponds to a range of radiation beam positions over a discrete time interval, wherein the discrete time interval is based on an average open-time and a modulation factor;
    generating a plurality of openings for each of the plurality of radiation beam delivery positional sections, each of the plurality of openings corresponding to one of a plurality of leaf pairs of the MLC, wherein two or more of the plurality of openings correspond to different widths;
    generating a plurality of leaf open-time fractions for each of the plurality of radiation beam delivery positional sections, each of the plurality of leaf open-time fractions corresponding to one of the plurality of leaf pairs of the MLC; and
    controlling, by a processing device, the plurality of leaf pairs of the MLC such that each leaf pair of the plurality of leaf pairs is opened to a corresponding opening of the plurality of openings for a corresponding leaf open-time fraction of the plurality of leaf open-time fractions during the discrete time interval corresponding to the range of radiation beam positions, while the radiation beam of the radiation treatment system is active.

2. The method of claim 1, wherein the plurality of radiation beam delivery positional sections corresponds to the radiation beam delivered from at least one of: a different position or a different direction.

3. The method of claim 1, wherein two or more of the plurality of leaf open-time fractions during the discrete time interval are different.

4. The method of claim 2, wherein the different direction remains constant while the different position follows a linear trajectory that sweeps the radiation beam over a length of a treatment target.

5. The method of claim 2, wherein the different directions are non-coplanar.

6. The method of claim 2, wherein the plurality of openings and the plurality of leaf open-time fractions form overlapping radiation fields of different intensities that combine to result in an intensity modulated fluence field delivered to a treatment target.

7. The method of claim 1, wherein the plurality of openings conform to an outline of a treatment target, projected back along the radiation beam to the MLC, and within a maximum range of travel of the plurality of leaf pairs within the MLC.

8. The method of claim 1, wherein the range of radiation beam positions is along an arc of a gantry of the radiation treatment system.

9. The method of claim 8, wherein the arc corresponds to approximately seven degrees of gantry rotation.

10. A radiation treatment delivery system, comprising:
    a linear accelerator (LINAC) to output a radiation beam at a distal end;
    a multileaf collimator (MLC), coupled with the distal end of the LINAC, wherein the MLC has two banks of leaves, organized into a plurality of opposing leaf pairs; and
    a processing device, operatively coupled to the LINAC and the MLC, to:
        control the plurality of leaf pairs of the MLC such that for each of a plurality of radiation beam delivery positional sections corresponding to a range of radiation beam positions over a discrete time interval, wherein each leaf pair of the plurality of opposing leaf pairs is open to a fixed opening for a fraction of time in the discrete time interval and closed for the remaining fraction of time in the discrete time interval, while the radiation beam of the radiation treatment system is active, wherein the discrete time interval is based on an average open-time and a modulation factor.

11. The system of claim 10, wherein the MLC is an electromagnetically actuated multileaf collimator (eMLC).

12. The system of claim 10, wherein the LINAC is mounted on a rotating gantry, and wherein radiation beams delivered from the range of radiation beam positions rotate around a treatment target.

13. The system of claim 12, wherein the treatment target is moved axially through a bore of the rotating gantry, and wherein the radiation beams delivered from the range of radiation beam positions follow a helical path about the treatment target.

14. The system of claim 10, wherein the LINAC and the MLC are mounted on a robotic arm, and wherein the radiation beam delivered from the range of radiation beam positions is non-coplanar.

15. The system of claim 10, wherein the fixed opening and the fraction of time form overlapping radiation fields of different intensities that combine to result in an intensity modulated fluence field delivered to a treatment target.

16. The system of claim 10, wherein the fixed opening conforms to an outline of a treatment target, projected back along the radiation beam to the MLC, and within a maximum range of travel of plurality of leaf pairs within the MLC.

17. The system of claim 10, wherein the plurality of radiation beam delivery positional sections corresponds to the radiation beam delivered from at least one of: a different position or a different direction, and wherein the at least one of: the different position or the different direction follows a helical trajectory about a treatment target.

18. The system of claim 10, wherein the system is a helical radiation treatment delivery system.

19. The system of claim 10, wherein the system is a robotic-based LINAC radiation treatment system.

20. The system of claim 10, wherein the system is gantry-based radiation treatment delivery system.

21. A non-transitory computer readable medium comprising instructions that, when executed by a processing device of a radiation treatment delivery system, cause the processing device to:
generate a plurality of radiation beam delivery positional sections to contain MLC leaf control instructions while a radiation beam is active, wherein each of the plurality of radiation beam delivery positional sections corresponds to a range of radiation beam positions over a discrete time interval, wherein the discrete time interval is based on an average open-time and a modulation factor;
generate a plurality of openings for each of the plurality of radiation beam delivery positional sections, each of the plurality of openings corresponding to one of a plurality of leaf pairs of the MLC;
generate a plurality of leaf open-time fractions for each of the plurality of radiation beam delivery positional sections, each of the plurality of leaf open-time fractions corresponding to one of the plurality of leaf pairs of the MLC; and
control, by the processing device, the plurality of leaf pairs of the MLC such that each leaf pair of the plurality of leaf pairs is opened to a corresponding opening of the plurality of openings for a corresponding leaf open-time fraction of the plurality of leaf open-time fractions during the discrete time interval corresponding to the range of radiation beam positions, while the radiation beam of the radiation treatment system is active.

22. The non-transitory computer readable medium of claim 21, wherein the plurality of radiation beam delivery positional sections corresponds to the radiation beam delivered from at least one of: a different position or a different direction.

23. The non-transitory computer readable medium of claim 22, wherein the at least one of: the different position or the different direction follows a helical trajectory about a treatment target.

24. The non-transitory computer readable medium of claim 22, wherein the different direction remains constant while the different position follows a linear trajectory that sweeps the radiation beam over a length of a treatment target.

25. The non-transitory computer readable medium of claim 22, wherein the different directions are non-coplanar.

26. The non-transitory computer readable medium of claim 21, wherein the plurality of openings and the plurality of leaf open-time fractions form overlapping radiation fields of different intensities that combine to result in an intensity modulated fluence field delivered to a treatment target.

27. The non-transitory computer readable medium of claim 21, wherein the plurality of openings conform to an outline of a treatment target, projected back along the radiation beam to the MLC, and within a maximum range of travel of the plurality of leaf pairs within the MLC.

28. The non-transitory computer readable medium of claim 21, wherein the range of radiation beam positions is along an arc of a gantry of the radiation treatment system.

29. The non-transitory computer readable medium of claim 28, wherein the arc corresponds to approximately seven degrees of gantry rotation.

* * * * *